United States Patent [19]
Ando et al.

[11] Patent Number: 5,422,359
[45] Date of Patent: Jun. 6, 1995

[54] α-AMINOKETONE DERIVATIVES

[75] Inventors: Ryoichi Ando, Kanagawa; Toshiro Sakaki, Tokyo; Yasuhiro Morinaka, Ibaraki; Chizuko Takahashi, Kanagawa; Yoshikuni Tamao, Tokyo, all of Japan

[73] Assignee: Mitsubishi Kasei Corporation, Tokyo, Japan

[21] Appl. No.: 171,692

[22] Filed: Dec. 22, 1993

[30] Foreign Application Priority Data

Dec. 25, 1992 [JP] Japan ................................. 4-346927

[51] Int. Cl.$^6$ .................. A61K 31/34; A61K 31/425; C07D 213/30; C07D 213/32
[52] U.S. Cl. .................................... 514/365; 514/374; 514/438; 514/471; 514/427; 514/629; 548/204; 548/236; 548/561; 549/77; 549/487; 564/192
[58] Field of Search .................. 549/77, 487; 548/204, 548/236, 561; 514/365, 374, 438, 471, 427, 629; 564/192

[56] References Cited
FOREIGN PATENT DOCUMENTS 0272671 6/1988 European Pat. Off. .
0525420 2/1993 European Pat. Off. .

OTHER PUBLICATIONS

Robinson et al., Chemical Abstracts, vol. 117, No. 3, 20 Jul. 1992 Abstract No. 22302m.
Ochi et al., Tetrahedron Letters, vol. 33, No. 49, pp. 7531–7534 (1992).

*Primary Examiner*—Richard L. Raymond
*Assistant Examiner*—Mary C. Cebulak
*Attorney, Agent, or Firm*—Wenderoth, Lind & Ponack

[57] ABSTRACT

Alpha-aminoketone derivatives of the present invention strongly inhibit thiol protease such as papain, cathepsin B, cathepsin H, cathepsin L and calpain or the like and have excellent properties in absorbance on oral administration, tissue distribution and cell membrane permeability. The alpha-aminoketone derivatives can thus be used as therapeutic agents for treating muscular dystrophy, amyotrophy, cardiac infarction, stroke, Alzheimer's disease, disturbance of consciousness or dyskinesia caused upon brain trauma, multiple sclerosis, peripheral nervous neuropathy, cataract, inflammation, allergosis, fulminant hepatitis, osteoporosis, hypercalcemia, breast carcinoma, prostatic carcinoma or prostatomegaly. They may also be used as therapeutic agents for suppressing growth of cancer cells, preventing metastasis of cancer or suppressing aggregation of plaques.

5 Claims, No Drawings

α-AMINOKETONE DERIVATIVES

FIELD OF THE INVENTION

This invention relates to novel α-aminoketone derivatives and, in particular, to novel α-aminoketone derivatives and their pharmaceutically acceptable salts which strongly inhibit thiol protease such as papain, cathepsin B, cathepsin H, cathepsin L and calpain or the like.

BACKGROUND OF THE INVENTION

In accordance with the elucidation of the in vivo activity of thiol protease such as papain, cathepsin B, cathepsin H, cathepsin L, calpain or the like, it has been found that their extraordinary hypersthenia causes various diseases. Further, in an increased number of the publications, thiol protease inhibitors are reported as being effective on such disease in animal models.

It is considered that thiol protease such as calpain, cathepsin B or the like takes part in the initial process such as disappearance of Z line through the decomposition of muscular fiber protein in the collapse of skeletal muscle as seen in muscular disease such as muscular Dystrophy, amyotrophy or the like [Taisha (Metabolism), 25, extra-edition "Taisha-byo Highlight (Metabolic Diseases Highlight)", 183 (1988)]. Furthermore, E-64-d, namely a thiol protease inhibitor, has been reported as having life-prolonging effect in experimental muscular dystrophy hamster [Journal of Pharmacobio dynamics, 10, 678 (1987)]. Accordingly, such thiol protease inhibitors are expected to be useful as therapeutic agents for the treatment of muscular dystrophy, amyotrophy or the like.

The main cause of the post-ischemic cellular disorder which occurs during ischemic diseases such as cardiac infarction, stroke and the like is active oxygen produced by xanthine oxidase. It has been reported that, during the ischemia, the increase in $Ca^{2+}$ concentration results in the activation of calpain which restrictively degrade xanthine dehydrogenase, a precursor of xanthine oxidase, to give xanthine oxidase [New England Journal of Medicine, 312, p.159, (1985)]. It has also been reported that the activation of calpain may directly cause the necrosis of myocardial cells or neurocytes [Saishin Igaku, 43, p.783, (1988)]. There have been reports that NCO-700, a calpain inhibitor, is effective on cardiac infarction when tested on animal models [Arzneimittel Forschung/Drug Research, 36, p.190, p.671, (1986)], and that E64-C inhibits the degradation of microtubule-associated protein after the brain ischemia [Brain Research, 526, p.177, (1990)]. These reports indicate that a calpain inhibitor can be useful for the treatment of ischemic diseases such as cardiac infarction, stroke and the like.

The cause of senile plaque which is found specifically in the brain of patients suffering from Alzheimer's disease is known to be the precipitated amyloid, a protein produced by the decomposition of an amyloid precursor protein (APP). Although APP does not give amyloid as a normal metabolite, it may be converted into amyloid under an abnormal metabolism where protease is extremely activated, and precipitated as senile plaque [Scientific American, (11), p.40, (1991)]. Therefore, protease inhibitor is expected to be useful for the treatment of Alzheimer's disease.

The activation of calpain has been observed in a brain trauma model of rabbit [Neurochemical Research, 16, p.483, (1991)]. It has also been observed that the administration of leupeptin, a calpain inhibitor, can protect axon in brain trauma models of rat [Journal of Neurosurgery, 65, p.92, (1986)]. Thus, calpain inhibitors are considered to be useful for improving the consciousness disturbance or motor disturbance caused by brain trauma.

It has also been reported that myelin-associated protein exists in dendrite of neurocytes is decomposed by calpain [Journal of Neurochemistry, 47, p.1007, (1986)], indicating that calpain inhibitors may be effective on diseases caused by the demyelination of neurocytes such as multiple sclerosis, peripheral nervous neuropathy and the like.

The main cause of the turbidity during cataract is hydrolytic products of a water-soluble protein crystalline by protease in lens. There has been observed the increase in calcium concentration in lens of cataractous animal models and some of human cataract [Investigative Ophthalmology & Visual Science, 28, p.1702, (1987); Experimental Eye Research, 34, p.413, (1982)]. The dominant protease contained in lens is calpain [Lens and Eye Toxicity Research, 6, p.725, (1989)]. These facts indicate that the abnormal sthenia of calpain can be one of the causes of cataract. There is a report that E-64, an inhibitor of calpain, is effective on cataract in animal models [Investigative Ophthalmology & Visual Science, 32, p.533, (1991)], indicating that calpain inhibitors can be useful in the treatment of cataract.

Neutrophils, which is deeply associated with inflammation, show the degranulation or production of superoxides in response to the stimulations by a chemotactic factor or phorbol ester through a mechanism appeared to be mediated by protein kinase C (PKC). Calpain participates in the activation of PKC in the manner where it promotes the degranulation and inhibits the production of superoxides [Journal of Biological Chemistry, 263, p.1915, (1988)]. In another report, the concentration of cathepsin B in macrophage in rat is 30 to 40 times that of leukocytes and neutrophils, and the concentration of enzyme in inflammatory macrophage is 6 times that of normal macrophage [Journal of Biochemistry, 98, p.87, (1985)]. These facts indicate that thiol protease inhibitors are useful as anti-inflammatory drugs.

The type I allergy reaction is mediated by immunoglobulin E (IgE) produced in the subject immunized with an antigen. Estatin A, a thiol protease inhibitor, has been reported to specifically inhibit the production of IgE without affecting on the production of IgG [The Journal of Antibiotics, 42, p.1362, (1989)]. Accordingly, thiol protease inhibitors are considered to be useful as antiallergic drugs.

In case of necrosis of hepatic cells, it is believed that impairment of the cell membrane leads to an increase in the permeability of $Ca^{2+}$, an increase in intracellular $Ca^{2+}$ concentration, an activation of calpain, and, as the result, the decomposition of its substrate such as skeletal protein takes place, which results in the death of cells. Accordingly, a calpain inhibitor can be used as a therapeutic agent for fulminant hepatitis.

Cathepsins such as dathepsin B and cathepsin L are involved in decomposition of bone collagen in osteoclast. It has been reported that administration of an inhibitor of cathepsins, E-64 or estatin A, to a rat which has an enhanced bone destruction by administration of parathyroid hormone leads to a decrease of calcium concentration and hydroxyproline concentration in blood [Biochemical and Biophysical Research Communication, 125, p.441, (1984): Japanese Patent Publication (kokai) No. 218610/1990]. Accordingly, it is believed that an inhibitor of cathepsins can be a therapeutic agent for osteoporosis, hypercalcemia and the like.

There exist, as a substrate for calpain, sex hormone receptors such as estrogen receptor and androgen receptor, and it is known that calpain activates these receptors. Accordingly, it is considered that an abnormal sthenia of calpain causes a disease which is suspected to be caused by an abnormal activation of the sex hormone receptors, for example, breast carcinoma, prostatic carcinoma or prostatomegaly. It is believed that an inhibitor for calpain can be a therapeutic agent for the above disease.

Receptors for epidermal growth factor (EGF) are also considered to be activated in association with the canceration of cells. It is known that calpain activates the EGF receptors as its substrate. Furthermore, it has been reported that calpain is activated in cells which have been infected with adult T cell human leukocyte virus (ATLV/HTLV-1) [Seikagaku, 57, p.1202, (1985)]. On the other hand, it is said that cathepsin B is greatly involved in a process of cancer metastasis because it accelerates decomposition of collagen which is a important step for the cancer metastasis or directly decompose collagen, and because it has a profound correlation with plasma membrane of neoplastic cells [Tumor Progression and Markers, p.47, (1982); Journal of Biological Chemistry, 256, p.8536, (1981)]. These facts suggest that a thiol protease inhibitor has an ability to suppress the growth of cancer cells and prevent the metastasis of cancer.

Activation of platelet causes the aggregation thereof which is a cause of thrombus. It has been reported that an inhibitor of calpain, E-64-d, suppressed aggregation of platelet caused by thrombin [Thrombosis Research, 57, p.847, (1990)]. Accordingly, the inhibitor of calpain can be used as an inhibitor against aggregation of platelet.

As described above, an abnormal sthenia of thiol protease causes various diseases and the validity of several thiol protease inhibitors in animal models has been reported. However, most of the known inhibitors, for example, epoxy succinate derivatives such as E-64 [Agricultural and Biological Chemistry, 42, p.529, (1978)], E-64-d [Journal of Biochemistry, 93, p.1305, (1983)], NCO-700 [Japanese Patent Publication (kokai) No. 126879/1983], and estatins A and B [The Journal of Antibiotics, 42, p.1362, (1989)]or α-substituted ketone of a peptide such as chloromethyl ketone [Journal of Biochemistry, 99, p.173, (1986)] and acyloxymethyl ketone [Biochemistry, 30, p.4678, (1991)] are irreversible inhibitors. It is generally said that the irreversible inhibitors are highly toxic because they are liable to react non-specifically with components constituting the living body, other than target enzymes. Therefore, there have been few compounds applicable to clinical use so far. Although peptidyl aldehydes such as leupeptin [The Journal of Antibiotics, 22, p.283, (1969)] or calpeptin [Journal of Enzyme Inhibition, 3, p.195, (1990)] are known as reversible inhibitors, they also have problems in chemical and in vivo stabilities, cell membrane permeabilities and the like.

SUMMARY OF THE INVENTION

The present inventors investigated into various compounds with the aim of developing reversible inhibitors against thiol protease, which have excellent properties in absorbance on oral administration, tissue distribution and cell membrane permeability, and have found that certain derivatives of ketone have such desired properties.

More particularly, the subject matter of the present invention is directed to an α-aminoketone derivative having the general formula (I) or a pharmaceutically acceptable salt thereof:

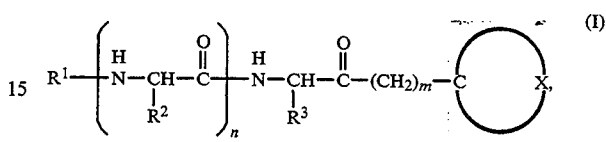

wherein, $R^1$ is hydrogen,

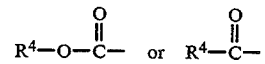

($R^4$ is $C_1$ to $C_{20}$ alkyl optionally substituted by one or more substituents selected from the group consisting of $C_3$ to $C_{15}$ cycloalkyl, $C_6$ to $C_{14}$ aryl optionally substituted by one or more substituents, a heterocyclic residue optionally substituted by one or more substituents, $C_3$ to $C_{15}$ cycloalkyloxy, $C_6$ to $C_{14}$ aryloxy optionally substituted by one or more substituents, $C_7$ to $C_{20}$ aralkyloxy optionally substituted by one or more substituents, and $C_6$ to $C_{14}$ arylthio optionally substituted by one or more substituents; $C_2$ to $C_{10}$ alkenyl optionally substituted by $C_6$ to $C_{14}$ aryl optionally substituted by one or more substituents; $C_6$ to $C_{14}$ aryl optionally substituted by one or more substituents; or a heterocyclic residue optionally substituted by one or more substituents), $R^2$ and $R^3$ are independently hydrogen or $C_1$ to $C_{20}$ alkyl optionally substituted by one or more substituents,

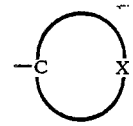

is a heterocyclic residue optionally substituted by one or more substituents, n is 0 or 1 and m is an integer of from 1 to 5.

DETAILED DESCRIPTION OF THE INVENTION

The present invention is described in detail below. The compounds according to the present invention are α-aminoketone derivatives having the general formula (I) or a pharmaceutically acceptable salt thereof:

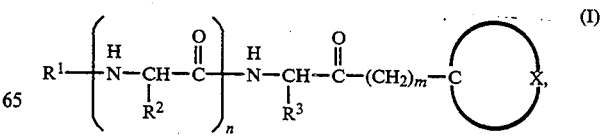

wherein, $R^1$ is hydrogen,

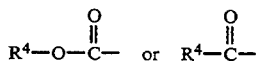

($R^4$ is selected from the group consisting of $C_1$ to $C_{20}$ alkyl (methyl, decyl, icocyl, etc.) optionally substituted by one or more substituents selected from the group consisting of $C_3$ to $C_{15}$ cycloalkyl (cyclopropyl, cyclononyl, cyclopentadecyl, etc.), $C_6$ to $C_{14}$ aryl (phenyl, naphthyl, anthryl, etc.) optionally substituted by one or more substituents (selected from the group (hereinafter, referred to as "Group 1") consisting of a halogen atom (a fluorine atom, a chlorine atom, a bromine atom, an iodine atom, etc.), $C_1$ to $C_5$ alkyl (methyl, propyl, pentyl, etc.), trifluoromethyl, $C_1$ to $C_5$ alkoxy (methoxy, propoxy, pentyloxy, etc.), $C_1$ to $C_5$ cyclic acetal residue (methylenedioxy, propylenedioxy, amylenedioxy, etc.), hydroxyl, $C_2$ to $C_6$ acyloxy (acetoxy, butyryloxy, valeryloxy, etc.), carboxyl, $C_2$ to $C_6$ alkoxycarbonyl (methoxycarbonyl, propoxycarbonyl, pentyloxycarbonyl, etc.), oxo, $C_2$ to $C_6$ acyl (acetyl, butyryl, valeryl, etc.), amino, $C_1$ to $C_5$ monoalkylamino (methylamino, propylamino, pentylamino, etc.), $C_2$ to $C_{10}$ dialkylamino (dimethylamino, methylpropyl, diisopropylamino, etc.), $C_2$ to $C_6$ acylamino (acetylamino, valerylamino, etc.), carbamoyl, $C_2$ to $C_6$ alkylcarbamoyl (methylcarbamoyl, propylcarbamoyl, pentylcarbamoyl, etc.) and $C_6$ to $C_{14}$ aryl (phenyl, naphthyl, anthryl, etc.)), a heterocyclic residue (a heterocyclic residue (hereinafter, referred to as "Group 2") having a ring of 5 to 10 atoms including 1 to 4 hetero atoms selected from the group consisting of oxygen atom, sulfur atom and nitrogen atom, (e.g., furan, dihydrofuran, tetrahydrofuran, pyran, dihydropyran, tetrahydropyran, benzofuran, isobenzofuran, chromene, chroman, isochroman, thiophene, benzothiophene, pyrrole, pyrroline, pyrrolidine, imidazole, imidazoline, imidazolidine, pyrazole, pyrazoline, pyrazolidine, triazole, tetrazole, pyridine, pyridineoxide, piperidine, pyrazine, piperazine, pyrimidine, pyridazine, indolizine, indole, indoline, isoindole, isoindoline, indazole, benzimidazole, purine, quinolizine, quinoline, phthalazine, naphtyridine, quinoxaline, quinazoline, cinnoline, pteridine, oxazole, oxazolidine, isooxazole, isoxazolidine, thiazole, thiazolidine, isothiazole, isothiazolidine, dioxane, dithian, morpholine, thiomorpholine) and optionally substituted by one or more substituents (selected from the Group 1), $C_3$ to $C_{15}$ cycloalkyloxy (cyclopropyloxy, cyclononyloxy, cyclopentadecyloxy, etc.), $C_6$ to $C_{14}$ aryloxy (phenoxy, naphthyloxy, anthryloxy, etc.) optionally substituted by one or more substituents (selected from the Group 1), $C_7$ to $C_{20}$ aralkyloxy (benzyloxy, phenylpentyloxy, naphthylmethoxy, naphthylethoxy, anthrylmethoxy, etc.) optionally substituted by one or more substituents (selected from the Group 1) and $C_6$ to $C_{14}$ arylthio (phenylthio, naphthylthio, anthrylthio, etc.) optionally substituted by one or more substituents (selected from the Group 1); $C_2$ to $C_{10}$ alkenyl (vinyl, hexeny, decenyl, etc.) optionally substituted by $C_6$ to $C_{14}$ aryl (phenyl, naphthyl, anthryl, etc.) optionally substituted by one or more substituents (selected from the Group 1); $C_6$ to $C_{14}$ aryl (phenyl, naphthyl, anthryl, etc.) optionally substituted by one or more substituents (selected from the Group 1)); or a heterocyclic residue (Group 2) optionally substituted by one or more substituents (selected from the Group 1), $R^2$ and $R^3$ are independently hydrogen or $C_1$ to $C_{20}$ alkyl(methyl, decyl, icocyl, etc.) optionally substituted by one or more substituent (selected from the Group 1), $$-C\bigcirc_x$$

is a heterocyclic residue (Group 2) optionally substituted by one or more substituent (selected from the Group 1), n is 0 or 1 and m is an integer of from 1 to 5.

Examples of the pharmaceutically acceptable salts are, in the presence of an acid group, metal salts such as a lithium salt, a sodium salt, a potassium salt, a magnesium salt and a calcium salt or ammonium salts such as an ammonium salt, a methyl ammonium salt, a dimethyl ammonium salt, a trimethyl ammonium salt and a dicyclohexyl ammonium salt and, in the presence of a base group, mineral acid salts such as hydrochloride, hydrobromide, sulfate, nitrate and phosphate or organic acid salts such as methane sulfonate, benzene sulfonate, para-toluene sulfonate, acetate, propionate, tartarate, fumatate, maleate, malate, oxalate, succinate, citrate, benzoate, mandelate, cinnamate and lactate.

The stereochemistry of the double bond of the α-aminoketone derivatives having the formula (I) is either one of E, Z and EZ. In addition, the stereochemical configuration of the asymmetric carbon is independently specified by either one of R, S and RS.

Examples of the α-aminoketone derivatives having the formula (I) are set forth in Table 1 and Table 2 below for n=0 and n=1, respectively.

TABLE 1

(n = 0)

| Comp. No. | $R^1$ | $R^3$ | m | $-C\bigcirc_x$ |
|---|---|---|---|---|
| 1 | (CH₃)₃COC(=O)— | H | 3 | (furan-2-yl with O) |
| 2 | C₆H₅—CH₂OC(=O)— | H | 3 | (furan-2-yl with O) |

TABLE 1-continued
(n = O)
| Comp. No. | R¹ | R³ | m | —C◯X |
|---|---|---|---|---|
| 3 | H | H | 3 | 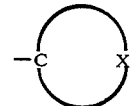 |
| 4 | (CH₃)₃COC(=O)— | H | 3 | 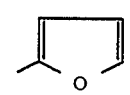 |
| 5 | C₆H₅CH₂OC(=O)— | H | 3 |  |
| 6 | H | H | 3 | 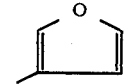 |
| 7 | (CH₃)₃COC(=O)— | H | 3 | 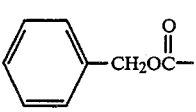 |
| 8 | C₆H₅CH₂OC(=O)— | H | 3 | 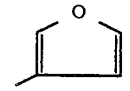 |
| 9 | H | H | 3 | 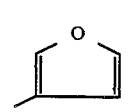 |
| 10 | (CH₃)₃COC(=O)— | H | 3 |  |
| 11 | C₆H₅CH₂OC(=O)— | H | 3 | 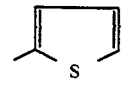 |
| 12 | H | H | 3 | 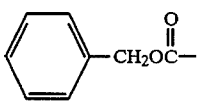 |
| 13 | (CH₃)₃COC(=O)— | CH₃— | 3 | 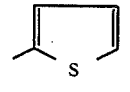 |
| 14 | C₆H₅CH₂OC(=O)— | CH₃— | 3 | 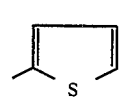 |
| 15 | H | CH₃— | 3 |  |

TABLE 1-continued
(n = 0)
| Comp. No. | R¹ | R³ | m | -C⟨⟩X |
|---|---|---|---|---|
| 16 | (CH₃)₃COC(=O)- | CH₃- | 3 | 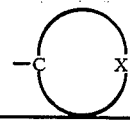 |
| 17 | PhCH₂OC(=O)- | CH₃- | 3 | 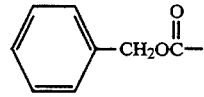 |
| 18 | H | CH₃- | 3 | 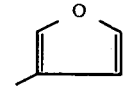 |
| 19 | (CH₃)₃COC(=O)- | CH₃- | 3 | 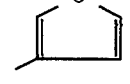 |
| 20 | PhCH₂OC(=O)- | CH₃- | 3 | 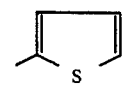 |
| 21 | H | CH₃- | 3 | 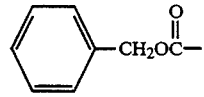 |
| 22 | (CH₃)₃COC(=O)- | CH₃- | 3 | 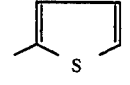 |
| 23 | PhCH₂OC(=O)- | CH₃- | 3 | 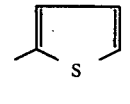 |
| 24 | H | CH₃- | 3 | 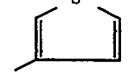 |
| 25 | (CH₃)₃COC(=O)- | (CH₃)₂CH- | 3 | 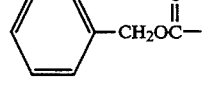 |
| 26 | PhCH₂OC(=O)- | (CH₃)₂CH- | 3 | 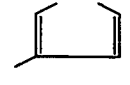 |
| 27 | H | (CH₃)₂CH- | 3 | 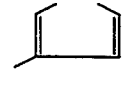 |
| 28 | (CH₃)₃COC(=O)- | (CH₃)₂CH- | 3 | 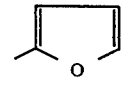 |

TABLE 1-continued
(n = O)
| Comp. No. | R¹ | R³ | m | 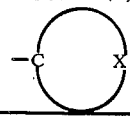 |
|---|---|---|---|---|
| 29 | 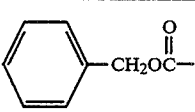 | $(CH_3)_2CH-$ | 3 |  |
| 30 | H | $(CH_3)_2CH-$ | 3 | 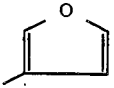 |
| 31 | $(CH_3)_3COC(O)-$ | $(CH_3)_2CH-$ | 3 | 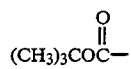 |
| 32 |  | $(CH_3)_2CH-$ | 3 | 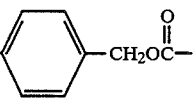 |
| 33 | H | $(CH_3)_2CH-$ | 3 | 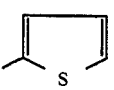 |
| 34 | $(CH_3)_3COC(O)-$ | $(CH_3)_2CH-$ | 3 | 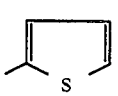 |
| 35 |  | $(CH_3)_2CH-$ | 3 | 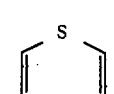 |
| 36 | H | $(CH_3)_2CH-$ | 3 | 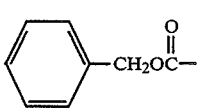 |
| 37 | $(CH_3)_3COC(O)-$ | $(CH_3)_2CHCH_2-$ | 3 | 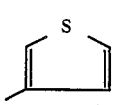 |
| 38 | 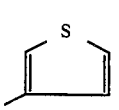 | $(CH_3)_2CHCH_2-$ | 3 | 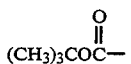 |
| 39 | H | $(CH_3)_2CHCH_2-$ | 3 |  |
| 40 | $(CH_3)_3COC(O)-$ | $(CH_3)_2CHCH_2-$ | 3 | 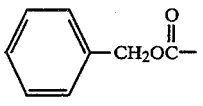 |
| 41 | 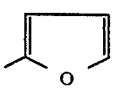 | $(CH_3)_2CHCH_2-$ | 3 | 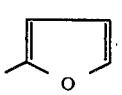 |

TABLE 1-continued
(n = O)
| Comp. No. | R¹ | R³ | m | -C X |
|---|---|---|---|---|
| 42 | H | $(CH_3)_2CHCH_2-$ | 3 | 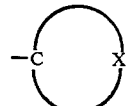 |
| 43 | $(CH_3)_3COC(=O)-$ | $(CH_3)_2CHCH_2-$ | 3 | 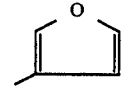 |
| 44 | $C_6H_5CH_2OC(=O)-$ | $(CH_3)_2CHCH_2-$ | 3 |  |
| 45 | H | $(CH_3)_2CHCH_2-$ | 3 | 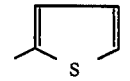 |
| 46 | $(CH_3)_3COC(=O)-$ | $(CH_3)_2CHCH_2-$ | 3 | 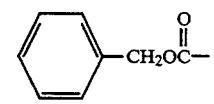 |
| 47 | $C_6H_5CH_2OC(=O)-$ | $(CH_3)_2CHCH_2-$ | 3 | 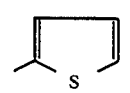 |
| 48 | H | $(CH_3)_2CHCH_2-$ | 3 | 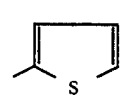 |
| 49 | $(CH_3)_3COC(=O)-$ | $CH_3CH_2CH_2CH_2-$ | 1 |  |
| 50 | $C_6H_5CH_2OC(=O)-$ | $CH_3CH_2CH_2CH_2-$ | 1 | 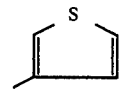 |
| 51 | H | $CH_3CH_2CH_2CH_2-$ | 1 | 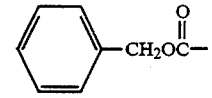 |
| 52 | $(CH_3)_2CHCH_2OC(=O)-$ | $CH_3CH_2CH_2CH_2-$ | 3 | 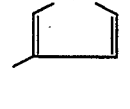 |
| 53 | $(CH_3)_3COC(=O)-$ | $CH_3CH_2CH_2CH_2-$ | 3 | 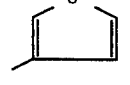 |
| 54 | $C_6H_{11}CH_2OC(=O)-$ | $CH_3CH_2CH_2CH_2-$ | 3 | 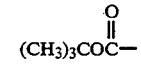 |

TABLE 1-continued (n = O)

| Comp. No. | R¹ | R³ | m | −C◯X |
|---|---|---|---|---|
| 55 | PhCH₂OC(O)− | CH₃CH₂CH₂CH₂− | 3 | 2-furyl |
| 56 | 4-CH₃O-C₆H₄-CH₂OC(O)− | CH₃CH₂CH₂CH₂− | 3 | 2-furyl |
| 57 | H | CH₃CH₂CH₂CH₂− | 3 | 2-furyl |
| 58 | PhOCH₂C(O)− | CH₃CH₂CH₂CH₂− | 3 | 2-furyl |
| 59 | 3-CH₃O-C₆H₄-OCH₂C(O)− | CH₃CH₂CH₂CH₂− | 3 | 2-furyl |
| 60 | 2,4-(CH₃O)₂-C₆H₃-CH=CH-C(O)CH₃ | CH₃CH₂CH₂CH₂− | 3 | 2-furyl |
| 61 | (CH₃)₃COC(O)− | CH₃CH₂CH₂CH₂− | 3 | 3-furyl |
| 62 | PhCH₂OC(O)− | CH₃CH₂CH₂CH₂− | 3 | 3-furyl |
| 63 | H | CH₃CH₂CH₂CH₂− | 3 | 3-furyl |
| 64 | (CH₃)₃COC(O)− | CH₃CH₂CH₂CH₂− | 3 | 2-thienyl |
| 65 | PhCH₂OC(O)− | CH₃CH₂CH₂CH₂− | 3 | 2-thienyl |
| 66 | H | CH₃CH₂CH₂CH₂− | 3 | 2-thienyl |

TABLE 1-continued (n = O)

| Comp. No. | R¹ | R³ | m | −C◯X |
|---|---|---|---|---|
| 67 | (CH₃)₃COC(=O)− | CH₃CH₂CH₂CH₂− | 3 | 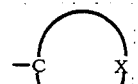 (S ring) |
| 68 | PhCH₂OC(=O)− | CH₃CH₂CH₂CH₂− | 3 | 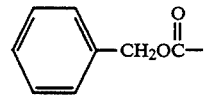 (S ring) |
| 69 | H | CH₃CH₂CH₂CH₂− | 3 | 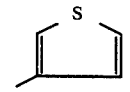 (S ring) |
| 70 | (CH₃)₃COC(=O)− | CH₃CH₂CH₂CH₂− | 2 | 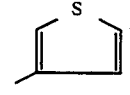 (O ring) |
| 71 | PhCH₂OC(=O)− | CH₃CH₂CH₂CH₂− | 2 | 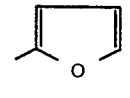 (O ring) |
| 72 | H | CH₃CH₂CH₂CH₂− | 2 | 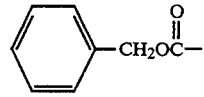 (O ring) |
| 73 | (CH₃)₃COC(=O)− | CH₃CH₂CH₂CH₂− | 4 | 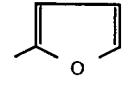 (O ring) |
| 74 | PhCH₂OC(=O)− | CH₃CH₂CH₂CH₂− | 4 | 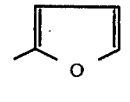 (O ring) |
| 75 | H | CH₃CH₂CH₂CH₂− | 4 | 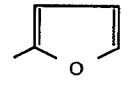 (O ring) |
| 76 | (CH₃)₃COC(=O)− | CH₃CH₂CH₂CH₂− | 5 | 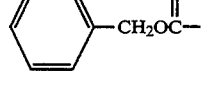 (O ring) |
| 77 | PhCH₂OC(=O)− | CH₃CH₂CH₂CH₂− | 5 | 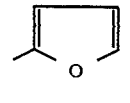 (O ring) |
| 78 | H | CH₃CH₂CH₂CH₂− | 5 | 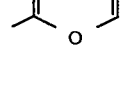 (O ring) |
| 79 | (CH₃)₃COC(=O)− | cyclohexyl-CH₂− | 3 | 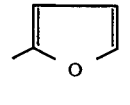 (O ring) |

TABLE 1-continued (n = 0)

| Comp. No. | R¹ | R³ | m | -C◯X |
|---|---|---|---|---|
| 80 | PhCH₂OC(O)- | cyclohexyl-CH₂- | 3 | furan (2-yl) |
| 81 | H | cyclohexyl-CH₂- | 3 | furan (2-yl) |
| 82 | (CH₃)₃COC(O)- | cyclohexyl-CH₂- | 3 | furan (3-yl) |
| 83 | PhCH₂OC(O)- | cyclohexyl-CH₂- | 3 | furan (3-yl) |
| 84 | H | cyclohexyl-CH₂- | 3 | furan (3-yl) |
| 85 | (CH₃)₃COC(O)- | cyclohexyl-CH₂- | 3 | thiophene (2-yl) |
| 86 | PhCH₂OC(O)- | cyclohexyl-CH₂- | 3 | thiophene (2-yl) |
| 87 | H | cyclohexyl-CH₂- | 3 | thiophene (2-yl) |
| 88 | (CH₃)₃COC(O)- | cyclohexyl-CH₂- | 3 | thiophene (3-yl) |
| 89 | PhCH₂OC(O)- | cyclohexyl-CH₂- | 3 | thiophene (3-yl) |
| 90 | H | cyclohexyl-CH₂- | 3 | thiophene (3-yl) |
| 91 | (CH₃)₃COC(O)- | CH₃SCH₂CH₂- | 3 | furan (2-yl) |

TABLE 1-continued
(n = O)
| Comp. No. | R¹ | R³ | m | -C◯X |
|---|---|---|---|---|
| 92 | PhCH₂OC(O)- | CH₃SCH₂CH₂- | 3 | 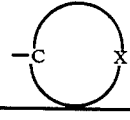 |
| 93 | H | CH₃SCH₂CH₂- | 3 | 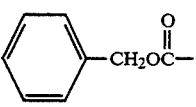 |
| 94 | (CH₃)₃COC(O)- | HOCH₂- | 3 | 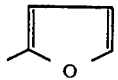 |
| 95 | PhCH₂OC(O)- | HOCH₂- | 3 | 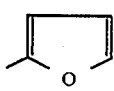 |
| 96 | H | HOCH₂- | 3 | 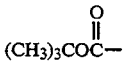 |
| 97 | (CH₃)₃COC(O)- | (CH₃)₃COCH₂- | 3 | 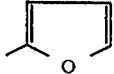 |
| 98 | PhCH₂OC(O)- | (CH₃)₃COCH₂- | 3 | 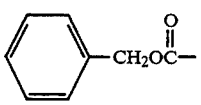 |
| 99 | H | (CH₃)₃COCH₂- | 3 | 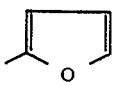 |
| 100 | (CH₃)₃COC(O)- | PhCH₂OCH₂- | 3 | 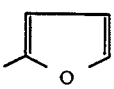 |
| 101 | PhCH₂OC(O)- | PhCH₂OCH₂- | 3 |  |
| 102 | H | PhCH₂OCH₂- | 3 | 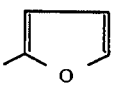 |
| 103 | (CH₃)₃COC(O)- | PhCH₂SCH₂- | 3 | 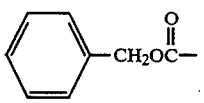 |
| 104 | PhCH₂OC(O)- | PhCH₂SCH₂- | 3 | 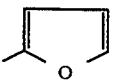 |

TABLE 1-continued (n = O)

| Comp. No. | R¹ | R³ | m | −C⟨X⟩ |
|---|---|---|---|---|
| 105 | H | C₆H₅−CH₂SCH₂− | 3 | furan |
| 106 | (CH₃)₃COC(O)− | (CH₃)₃COCCH₂CH₂− (with C=O) | 3 | furan |
| 107 | C₆H₅CH₂OC(O)− | (CH₃)₃COCCH₂CH₂− | 3 | furan |
| 108 | H | (CH₃)₃COCCH₂CH₂− | 3 | furan |
| 109 | (CH₃)₃COC(O)− | HOOCCH₂CH₂− | 3 | furan |
| 110 | C₆H₅CH₂OC(O)− | HOOCCH₂CH₂− | 3 | furan |
| 111 | H | HOOCCH₂CH₂− | 3 | furan |
| 112 | (CH₃)₃COC(O)− | H₂NCCH₂CH₂− (C=O) | 3 | furan |
| 113 | C₆H₅CH₂OC(O)− | H₂NCCH₂CH₂− | 3 | furan |
| 114 | H | H₂NCCH₂CH₂− | 3 | furan |
| 115 | (CH₃)₃COC(O)− | (CH₃)₃COCNH(CH₂)₄− | 3 | furan |
| 116 | C₆H₅CH₂OC(O)− | (CH₃)₃COCNH(CH₂)₄− | 3 | furan |
| 117 | H | (CH₃)₃COCNH(CH₂)₄− | 3 | furan |

TABLE 1-continued (n = O)

| Comp. No. | R¹ | R³ | m | —C◯X |
|---|---|---|---|---|
| 118 | (CH₃)₃COC(=O)— | H₂NCH₂CH₂CH₂CH₂— | 3 | furan |
| 119 | PhCH₂OC(=O)— | H₂NCH₂CH₂CH₂CH₂— | 3 | furan |
| 120 | H | H₂NCH₂CH₂CH₂CH₂— | 3 | furan |
| 121 | (CH₃)₃CHCH₂OC(=O)— | PhCH₂— | 3 | furan |
| 122 | (CH₃)₃COC(=O)— | PhCH₂— | 3 | furan |
| 123 | cyclohexyl-CH₂OC(=O)— | PhCH₂— | 3 | furan |
| 124 | PhCH₂OC(=O)— | PhCH₂— | 3 | furan |
| 125 | 3-CH₃O-C₆H₄-CH₂OC(=O)— | PhCH₂— | 3 | furan |
| 126 | 4-CH₃O-C₆H₄-CH₂OC(=O)— | PhCH₂— | 3 | furan |
| 127 | H | PhCH₂— | 3 | furan |
| 128 | 1-naphthyl-CH₂C(=O)— | PhCH₂— | 3 | furan |

TABLE 1-continued
(n = O)
| Comp. No. | R¹ | R³ | m | −C⌒X |
|---|---|---|---|---|
| 129 | 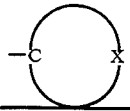 | 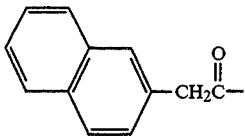 | 3 | 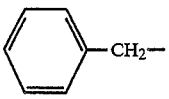 |
| 130 | 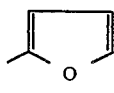 | 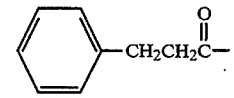 | 3 | 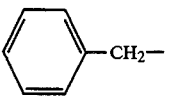 |
| 131 | 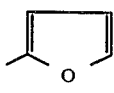 | 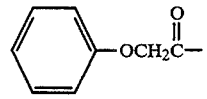 | 3 | 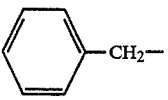 |
| 132 | 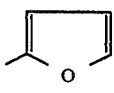 | 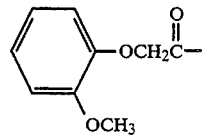 | 3 | 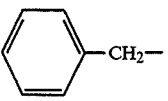 |
| 133 | 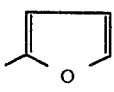 | 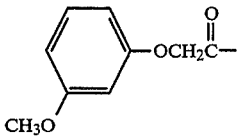 | 3 | 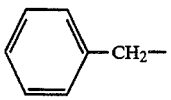 |
| 134 | 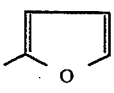 |  | 3 | 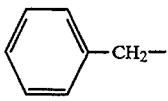 |
| 135 | 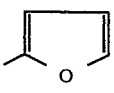 | 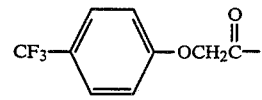 | 3 | 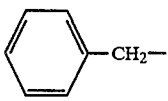 |
| 136 | 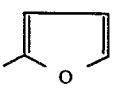 | 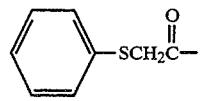 | 3 | 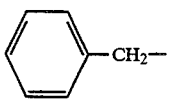 |
| 137 | 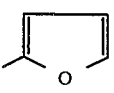 | 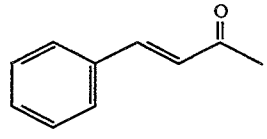 | 3 | 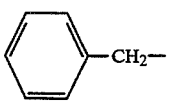 |
| 138 | 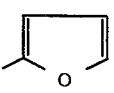 | 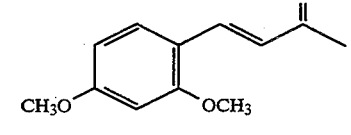 | 3 | 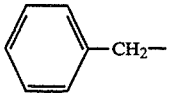 |
| 139 | 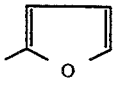 | 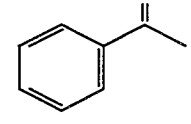 | 3 | 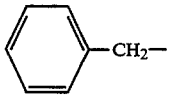 |

TABLE 1-continued
(n = O)
| Comp. No. | R¹ | R³ | m | −C⌒X |
|---|---|---|---|---|
| 140 | 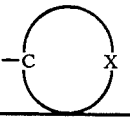 | 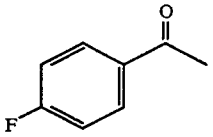 | 3 | 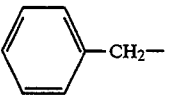 |
| 141 | 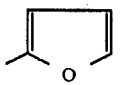 | 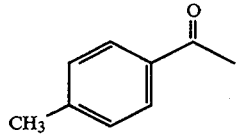 | 3 | 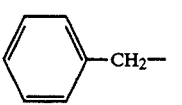 |
| 142 | 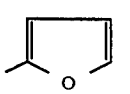 | 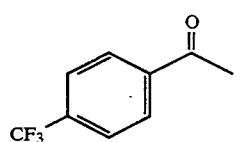 | 3 | 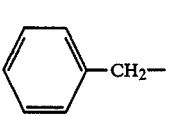 |
| 143 |  | 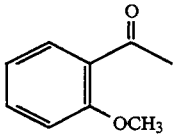 | 3 | 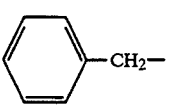 |
| 144 | 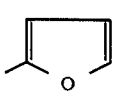 | 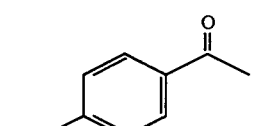 | 3 | 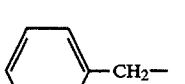 |
| 145 | 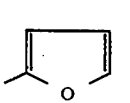 | 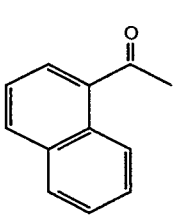 | 3 | 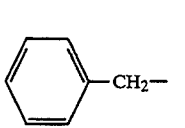 |
| 146 | 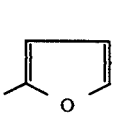 | 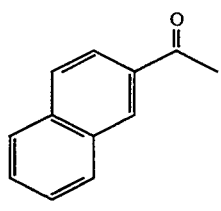 | 3 | 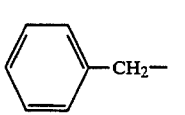 |
| 147 |  | 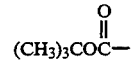 | 3 | 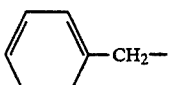 |
| 148 | 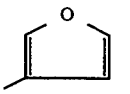 | 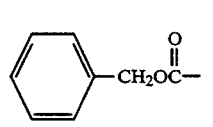 | 3 | 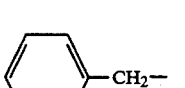 |
| 149 | H | 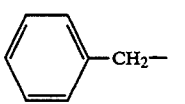 | 3 | 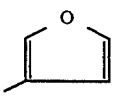 |

TABLE 1-continued (n = 0)

| Comp. No. | R¹ | R³ | m | —C⟨X⟩ (ring) |
|---|---|---|---|---|
| 150 | (CH₃)₃COC(O)— | C₆H₅CH₂— | 3 | 2-thienyl (S at position, attached at 2) |
| 151 | C₆H₅CH₂OC(O)— | C₆H₅CH₂— | 3 | 2-thienyl |
| 152 | H | C₆H₅CH₂— | 3 | 2-thienyl |
| 153 | (CH₃)₃COC(O)— | C₆H₅CH₂— | 3 | 3-thienyl |
| 154 | C₆H₅CH₂OC(O)— | C₆H₅CH₂— | 3 | 3-thienyl |
| 155 | H | C₆H₅CH₂— | 3 | 3-thienyl |
| 156 | C₆H₅OCH₂C(O)— | C₆H₅CH₂— | 3 | 3-thienyl |
| 157 | 3-CH₃O-C₆H₄-OCH₂C(O)— | C₆H₅CH₂— | 3 | 3-thienyl |
| 158 | (CH₃)₃COC(O)— | C₆H₅CH₂— | 3 | oxazolyl (N=C–O) |
| 159 | C₆H₅CH₂OC(O)— | C₆H₅CH₂— | 3 | oxazolyl |
| 160 | H | C₆H₅CH₂— | 3 | oxazolyl |
| 161 | (CH₃)₃COC(O)— | C₆H₅CH₂— | 3 | thiazolyl (N=C–S) |

TABLE 1-continued (n = O)

| Comp. No. | R¹ | R³ | m | -C⟨⟩X |
|---|---|---|---|---|
| 162 | PhCH₂OC(O)– | PhCH₂– | 3 | thiazoline (N=C, S) |
| 163 | H | PhCH₂– | 3 | thiazoline (N=C, S) |
| 164 | (CH₃)₃COC(O)– | PhCH₂– | 3 | thiophene with Cl |
| 165 | PhCH₂OC(O)– | PhCH₂– | 3 | thiophene with Cl |
| 166 | H | PhCH₂– | 3 | thiophene with Cl |
| 167 | (CH₃)₃COC(O)– | PhCH₂– | 3 | CH₃-furan |
| 168 | PhCH₂OC(O)– | PhCH₂– | 3 | CH₃-furan |
| 169 | H | PhCH₂– | 3 | CH₃-furan |
| 170 | (CH₃)₃COC(O)– | 4-F-C₆H₄-CH₂– | 3 | furan |
| 171 | PhCH₂OC(O)– | 4-F-C₆H₄-CH₂– | 3 | furan |
| 172 | H | 4-F-C₆H₄-CH₂– | 3 | furan |
| 173 | (CH₃)₃COC(O)– | 4-Cl-C₆H₄-CH₂– | 3 | furan |

TABLE 1-continued
(n = O)
| Comp. No. | R¹ | R³ | m | -C⟨X⟩ |
|---|---|---|---|---|
| 174 | C₆H₅CH₂OC(O)- | 4-Cl-C₆H₄-CH₂- | 3 | 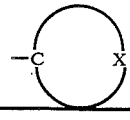 |
| 175 | H | 4-Cl-C₆H₄-CH₂- | 3 | 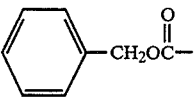 |
| 176 | (CH₃)₃CC(O)- | 4-(CH₃)₃CO-C₆H₄-CH₂- | 3 | 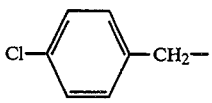 |
| 177 | C₆H₅CH₂OC(O)- | 4-(CH₃)₃CO-C₆H₄-CH₂- | 3 | 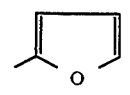 |
| 178 | H | 4-(CH₃)₃CO-C₆H₄-CH₂- | 3 | 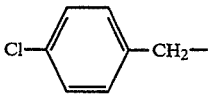 |
| 179 | (CH₃)₃CC(O)- | 4-HO-C₆H₄-CH₂- | 3 | 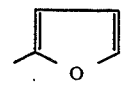 |
| 180 | C₆H₅CH₂OC(O)- | 4-HO-C₆H₄-CH₂- | 3 | 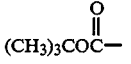 |
| 181 | H | 4-HO-C₆H₄-CH₂- | 3 | 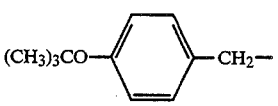 |
| 182 | (CH₃)₃CC(O)- | 4-CH₃O-C₆H₄-CH₂- | 3 | 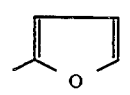 |
| 183 | C₆H₅CH₂OC(O)- | 4-CH₃O-C₆H₄-CH₂- | 3 | 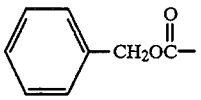 |
| 184 | H | 4-CH₃O-C₆H₄-CH₂- | 3 | 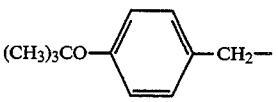 |
| 185 | (CH₃)₃CC(O)- | C₆H₅-CH₂CH₂- | 3 | 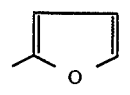 |

TABLE 1-continued
(n = O)
| Comp. No. | R¹ | R³ | m | 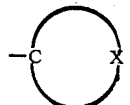 |
|---|---|---|---|---|
| 186 | 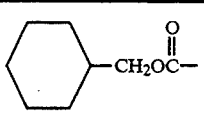 | 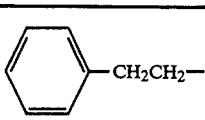 —CH₂CH₂— | 3 | 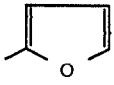 |
| 187 | 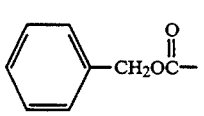 | —CH₂CH₂— | 3 | 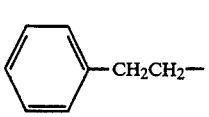 |
| 188 | H | —CH₂CH₂— | 3 | 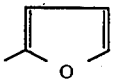 |
| 189 | 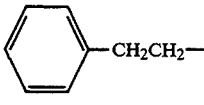 | —CH₂CH₂— | 3 | 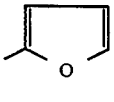 |
| 190 | 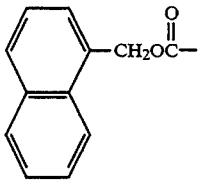 | —CH₂CH₂— | 3 | 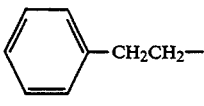 |
| 191 | 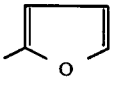 | —CH₂CH₂— | 3 | 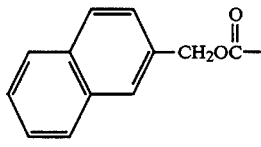 |
| 192 | 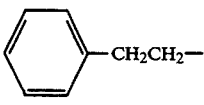 | —CH₂CH₂— | 3 | 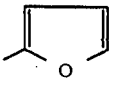 |
| 193 | 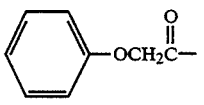 | —CH₂CH₂— | 3 | 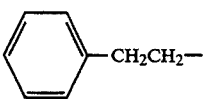 |
| 194 | (CH₃)₃CO$\overset{O}{\overset{\|}{C}}$— | —CH₂CH₂— | 3 | 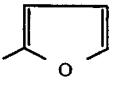 |
| 195 | 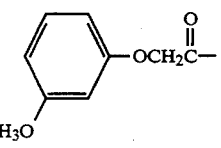 | —CH₂CH₂— | 3 | 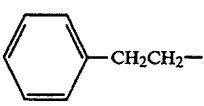 |
| 196 | H | —CH₂CH₂— | 3 | 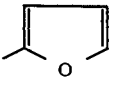 |

TABLE 1-continued
(n = 0)

| Comp. No. | R¹ | R³ | m | 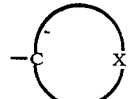 |
|---|---|---|---|---|
| 197 | (CH₃)₃COC(O)— | phenyl-CH₂CH₂— | 3 | 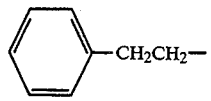 thiophene (2-yl) |
| 198 | phenyl-CH₂OC(O)— | phenyl-CH₂CH₂— | 3 | 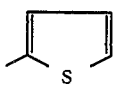 thiophene (2-yl) |
| 199 | H | phenyl-CH₂CH₂— | 3 | 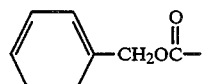 thiophene (2-yl) |
| 200 | (CH₃)₃COC(O)— | phenyl-CH₂CH₂— | 3 | 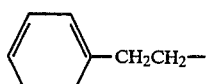 thiophene (3-yl) |
| 201 | phenyl-CH₂OC(O)— | phenyl-CH₂CH₂— | 3 | 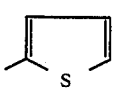 thiophene (3-yl) |
| 202 | H | phenyl-CH₂CH₂— | 3 | 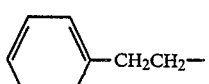 thiophene (3-yl) |
| 203 | (CH₃)₃COC(O)— | 1-naphthyl-CH₂— | 3 | 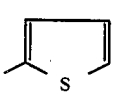 furan (2-yl) |
| 204 | phenyl-CH₂OC(O)— | 1-naphthyl-CH₂— | 3 | 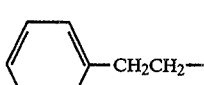 furan (2-yl) |
| 205 | H | 1-naphthyl-CH₂— | 3 | 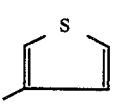 furan (2-yl) |
| 206 | (CH₃)₃COC(O)— | 2-naphthyl-CH₂— | 3 | 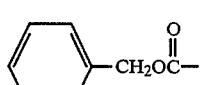 furan (2-yl) |

TABLE 1-continued
(n = 0)
| Comp. No. | R¹ | R³ | m | —C⟨ring⟩X |
|---|---|---|---|---|
| 207 | 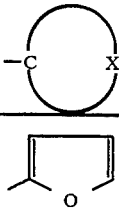 | 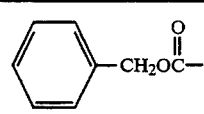 | 3 | 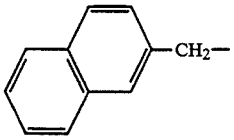 |
| 208 | H | 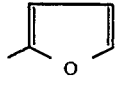 | 3 | 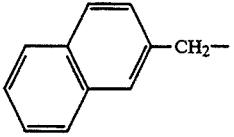 |
TABLE 2
(n = 1)
| Comp. No. | R¹ | R² | R³ | m | —C⟨ring⟩X |
|---|---|---|---|---|---|
| 209 | 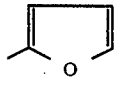 | $(CH_3)_2CHCH_2-$ | H | 3 | 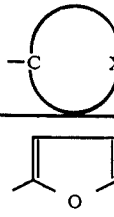 |
| 210 | 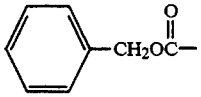 | $(CH_3)_2CHCH_2-$ | H | 3 | 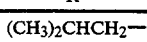 |
| 211 | 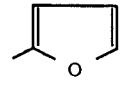 | $(CH_3)_2CHCH_2-$ | H | 3 | 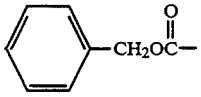 |
| 212 |  | $(CH_3)_2CHCH_2-$ | H | 3 | 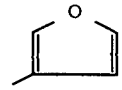 |
| 213 | 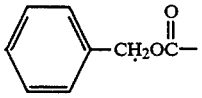 | $(CH_3)_2CHCH_2-$ | $CH_3-$ | 3 |  |
| 214 | $(CH_3)_3COC(O)-$ | 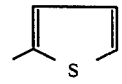 | $CH_3-$ | 3 | 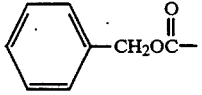 |
| 215 | 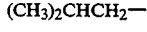 | 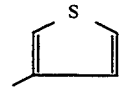 | $CH_3-$ | 3 | 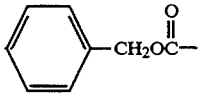 |
| 216 |  | 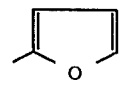 | $CH_3-$ | 3 | 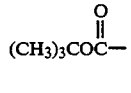 |

TABLE 2-continued (n = 1)

| Comp. No. | R¹ | R² | R³ | m | −C⟨X⟩ |
|---|---|---|---|---|---|
| 217 | H | 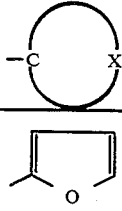 PhCH₂− | CH₃− | 3 | 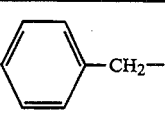 furan |
| 218 | 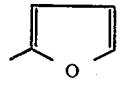 1-naphthyl-CH₂C(O)− | 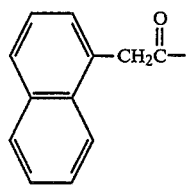 PhCH₂− | CH₃− | 3 | 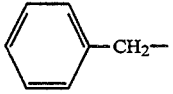 furan |
| 219 | 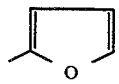 PhOCH₂C(O)− | 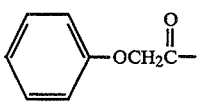 PhCH₂− | CH₃− | 3 | 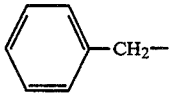 furan |
| 220 | 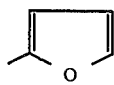 4-CH₃O-C₆H₄-OCH₂C(O)− | 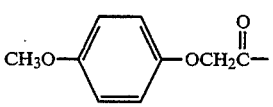 PhCH₂− | CH₃− | 3 | 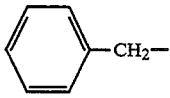 furan |
| 221 | 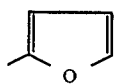 4-CF₃-C₆H₄-OCH₂C(O)− | 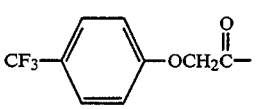 PhCH₂− | CH₃− | 3 | 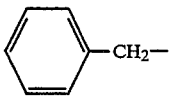 furan |
| 222 | 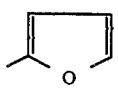 PhC(O)− (methyl ketone) | 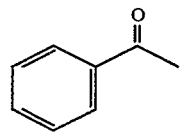 PhCH₂− | CH₃− | 3 | 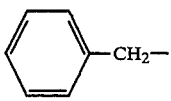 furan |
| 223 | 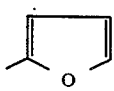 2-F-C₆H₄-C(O)CH₃ | 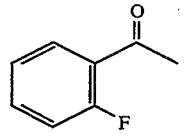 PhCH₂− | CH₃− | 3 | 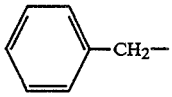 furan |
| 224 | 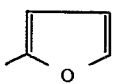 4-F-C₆H₄-C(O)CH₃ | 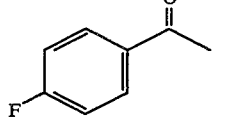 PhCH₂− | CH₃− | 3 | 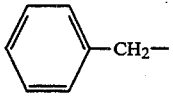 furan |
| 225 | 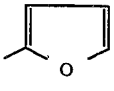 4-CF₃-C₆H₄-C(O)CH₃ | 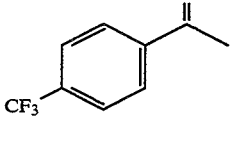 PhCH₂− | CH₃− | 3 | 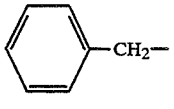 furan |
| 226 | 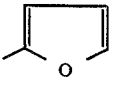 PhCH₂OC(O)− | 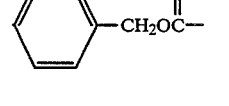 PhCH₂− | CH₃− | 3 | 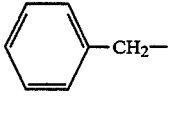 3-furyl |
| 227 | 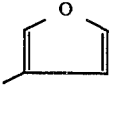 PhCH₂OC(O)− | 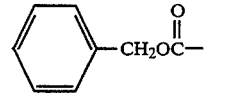 PhCH₂− | CH₃− | 3 | 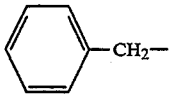 thienyl |

TABLE 2-continued (n = 1)

| Comp. No. | R¹ | R² | R³ | m | —C⟨X |
|---|---|---|---|---|---|
| 228 | (CH₃)₃COC(O)— | C₆H₅CH₂— | CH₃— | 3 | 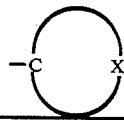 thiophene |
| 229 | C₆H₅CH₂OC(O)— | C₆H₅CH₂— | CH₃— | 3 | 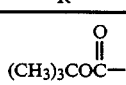 thiophene |
| 230 | H | C₆H₅CH₂— | CH₃— | 3 | 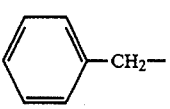 thiophene |
| 231 | C₆H₅OCH₂C(O)— | C₆H₅CH₂— | CH₃— | 3 | 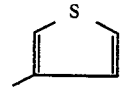 thiophene |
| 232 | 4-CH₃O-C₆H₄-OCH₂C(O)— | C₆H₅CH₂— | CH₃— | 3 | 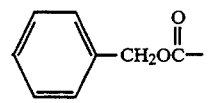 thiophene |
| 233 | 4-CF₃-C₆H₄-OCH₂C(O)— | C₆H₅CH₂— | CH₃— | 3 | 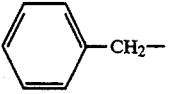 thiophene |
| 234 | C₆H₅CH₂OC(O)— | (CH₃)₂CHCH₂— | (CH₃)₂CH— | 3 | 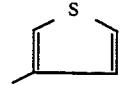 furan |
| 235 | C₆H₅CH₂OC(O)— | (CH₃)₂CHCH₂— | (CH₃)₂CH— | 3 | 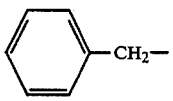 furan |
| 236 | C₆H₅CH₂OC(O)— | (CH₃)₂CHCH₂— | (CH₃)₂CH— | 3 | 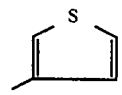 thiophene |
| 237 | C₆H₅CH₂OC(O)— | (CH₃)₂CHCH₂— | (CH₃)₂CH— | 3 | 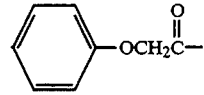 thiophene |
| 238 | C₆H₅CH₂OC(O)— | (CH₃)₂CHCH₂— | (CH₃)₂CHCH₂— | 3 | 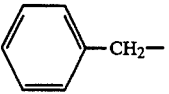 furan |
| 239 | C₆H₅CH₂OC(O)— | (CH₃)₂CHCH₂— | (CH₃)₂CHCH₂— | 3 | 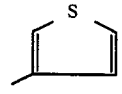 furan |

TABLE 2-continued
(n = 1)
| Comp. No. | R¹ | R² | R³ | m | −C⌬X |
|---|---|---|---|---|---|
| 240 | 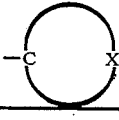 | $(CH_3)_2CHCH_2-$ | $CH_3CH_2CH_2CH_2-$ | 1 | 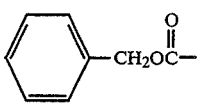 |
| 241 | 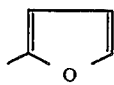 | $(CH_3)_2CHCH_2-$ | $CH_3CH_2CH_2CH_2-$ | 1 | 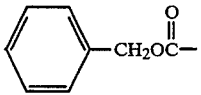 |
| 242 | 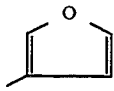 | $(CH_3)_2CHCH_2-$ | $CH_3CH_2CH_2CH_2-$ | 1 | 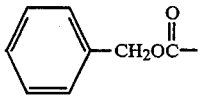 |
| 243 | 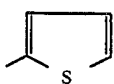 | $(CH_3)_2CHCH_2-$ | $CH_3CH_2CH_2CH_2-$ | 1 | 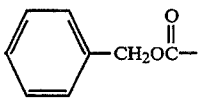 |
| 244 | 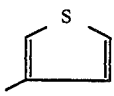 | $(CH_3)_2CHCH_2-$ | $CH_3CH_2CH_2CH_2-$ | 2 | 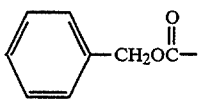 |
| 245 | 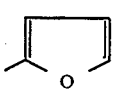 | $(CH_3)_2CHCH_2-$ | $CH_3CH_2CH_2CH_2-$ | 2 | 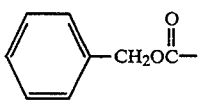 |
| 246 | 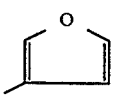 | $(CH_3)_2CHCH_2-$ | $CH_3CH_2CH_2CH_2-$ | 2 | 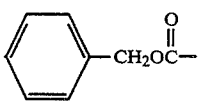 |
| 247 | 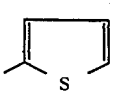 | $(CH_3)_2CHCH_2-$ | $CH_3CH_2CH_2CH_2-$ | 2 | 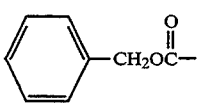 |
| 248 | 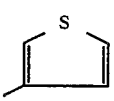 | H | $CH_3CH_2CH_2CH_2-$ | 3 | 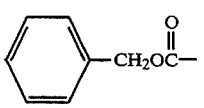 |
| 249 | 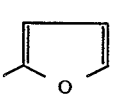 | $CH_3-$ | $CH_3CH_2CH_2CH_2-$ | 3 | 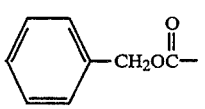 |
| 250 | 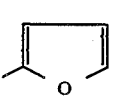 | $(CH_3)_2CH-$ | $CH_3CH_2CH_2CH_2-$ | 3 | 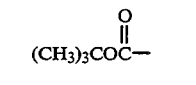 |
| 251 | 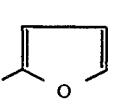 | $(CH_3)_2CH-$ | $CH_3CH_2CH_2CH_2-$ | 3 | 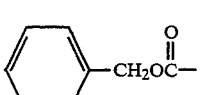 |
| 252 | H | $(CH_3)_2CH-$ | $CH_3CH_2CH_2CH_2-$ | 3 | 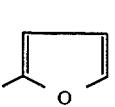 |

TABLE 2-continued
(n = 1)
| Comp. No. | R¹ | R² | R³ | m | −C⌒X |
|---|---|---|---|---|---|
| 253 | 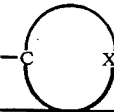 | $(CH_3)_2CH-$ | $CH_3CH_2CH_2CH_2-$ | 3 | 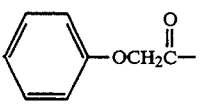 |
| 254 | 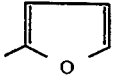 | $(CH_3)_2CH-$ | $CH_3CH_2CH_2CH_2-$ | 3 | 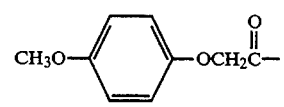 |
| 255 | 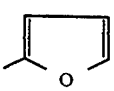 | $(CH_3)_2CHCH_2-$ | $CH_3CH_2CH_2CH_2-$ | 3 | 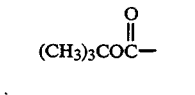 |
| 256 |  | $(CH_3)_2CHCH_2-$ | $CH_3CH_2CH_2CH_2-$ | 3 | 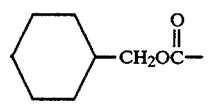 |
| 257 | 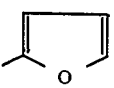 | $(CH_3)_2CHCH_2-$ | $CH_3CH_2CH_2CH_2-$ | 3 | 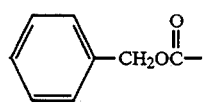 |
| 258 | 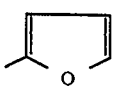 | $(CH_3)_2CHCH_2-$ | $CH_3CH_2CH_2CH_2-$ | 3 | 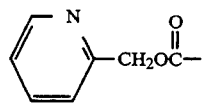 |
| 259 |  | $(CH_3)_2CHCH_2-$ | $CH_3CH_2CH_2CH_2-$ | 3 | 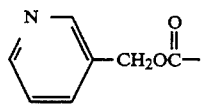 |
| 260 |  | $(CH_3)_2CHCH_2-$ | $CH_3CH_2CH_2CH_2-$ | 3 | 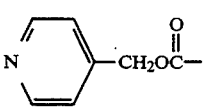 |
| 261 | H | $(CH_3)_2CHCH_2-$ | $CH_3CH_2CH_2CH_2-$ | 3 |  |
| 262 |  | $(CH_3)_2CHCH_2-$ | $CH_3CH_2CH_2CH_2-$ | 3 | 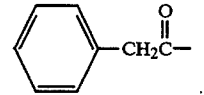 |
| 263 | 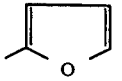 | $(CH_3)_2CHCH_2-$ | $CH_3CH_2CH_2CH_2-$ | 3 | 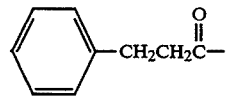 |
| 264 | 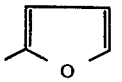 | $(CH_3)_2CHCH_2-$ | $CH_3CH_2CH_2CH_2-$ | 3 | 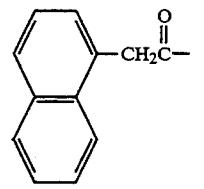 |

TABLE 2-continued
(n = 1)
| Comp. No. | R¹ | R² | R³ | m | -C-X ring |
|---|---|---|---|---|---|
| 265 | 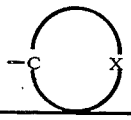 | (CH₃)₂CHCH₂— | CH₃CH₂CH₂CH₂— | 3 | 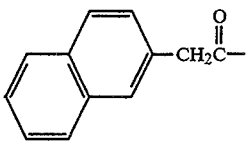 |
| 266 | 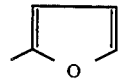 | (CH₃)₂CHCH₂— | CH₃CH₂CH₂CH₂— | 3 | 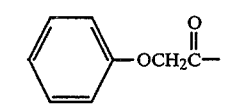 |
| 267 | 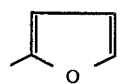 | (CH₃)₂CHCH₂— | CH₃CH₂CH₂CH₂— | 3 | 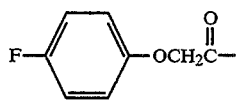 |
| 268 | 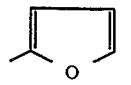 | (CH₃)₂CHCH₂— | CH₃CH₂CH₂CH₂— | 3 | 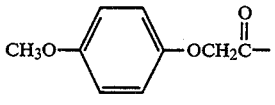 |
| 269 | 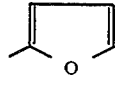 | (CH₃)₂CHCH₂— | CH₃CH₂CH₂CH₂— | 3 | 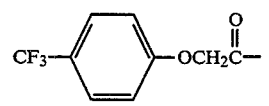 |
| 270 | 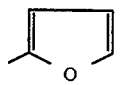 | (CH₃)₂CHCH₂— | CH₃CH₂CH₂CH₂— | 3 | 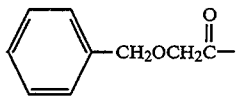 |
| 271 | 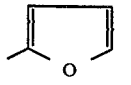 | (CH₃)₂CHCH₂— | CH₃CH₂CH₂CH₂— | 3 | 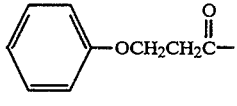 |
| 272 | 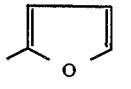 | (CH₃)₂CHCH₂— | CH₃CH₂CH₂CH₂— | 3 | 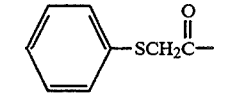 |
| 273 | 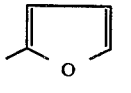 | (CH₃)₂CHCH₂— | CH₃CH₂CH₂CH₂— | 3 | 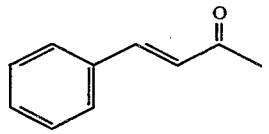 |
| 274 | 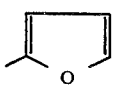 | (CH₃)₂CHCH₂— | CH₃CH₂CH₂CH₂— | 3 | 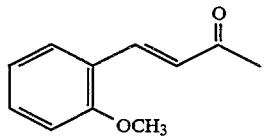 |
| 275 | 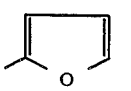 | (CH₃)₂CHCH₂— | CH₃CH₂CH₂CH₂— | 3 | 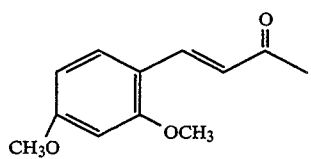 |

TABLE 2-continued
(n = 1)
| Comp. No. | R¹ | R² | R³ | m | −C⌒X |
|---|---|---|---|---|---|
| 276 | 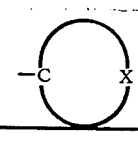 | (CH₃)₂CHCH₂— | CH₃CH₂CH₂— | 3 | 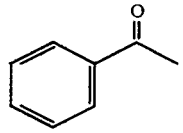 |
| 277 | 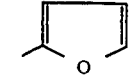 | (CH₃)₂CHCH₂— | CH₃CH₂CH₂— | 3 | 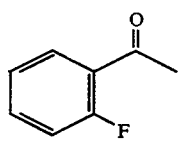 |
| 278 | 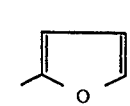 | (CH₃)₂CHCH₂— | | 3 | 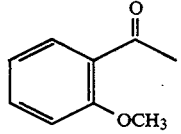 |
| 279 | 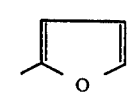 | (CH₃)₂CHCH₂— | CH₃CH₂CH₂— | 3 | 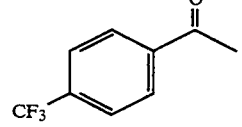 |
| 280 | 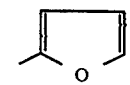 | (CH₃)₂CHCH₂— | CH₃CH₂CH₂— | 3 | 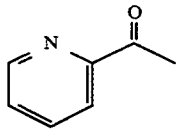 |
| 281 | 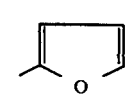 | (CH₃)₂CHCH₂— | CH₃CH₂CH₂— | 3 | 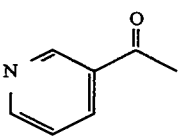 |
| 282 | 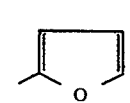 | (CH₃)₂CHCH₂— | CH₃CH₂CH₂— | 3 | 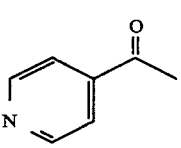 |
| 283 | 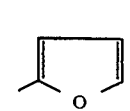 | (CH₃)₂CHCH₂— | CH₃CH₂CH₂— | 3 | 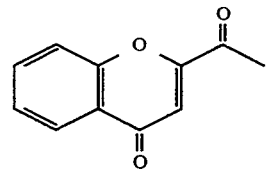 |
| 284 | 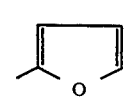 | (CH₃)₂CHCH₂— | CH₃CH₂CH₂— | 3 | 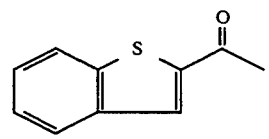 |
| 285 | 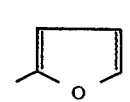 | (CH₃)₂CHCH₂— | CH₃CH₂CH₂— | 3 | 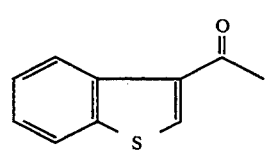 |

5,422,359

TABLE 2-continued (n = 1)

| Comp. No. | R¹ | R² | R³ | m | −C⟨X⟩ |
|---|---|---|---|---|---|
| 286 | PhCH₂OC(O)− | CH₃CH₂CH₂CH₂− | CH₃CH₂CH₂CH₂− | 3 | 2,5-dihydrofuran |
| 287 | PhCH₂OC(O)− | cyclohexyl-CH₂− | CH₃CH₂CH₂CH₂− | 3 | 2,5-dihydrofuran |
| 288 | PhCH₂OC(O)− | CH₃SCH₂CH₂− | CH₃CH₂CH₂CH₂− | 3 | 2,5-dihydrofuran |
| 289 | PhCH₂OC(O)− | CH₃OC(O)CH₂CH₂ | CH₃CH₂CH₂CH₂− | 3 | 2,5-dihydrofuran |
| 290 | PhCH₂OC(O)− | HOC(O)CH₂CH₂− | CH₃CH₂CH₂CH₂− | 3 | 2,5-dihydrofuran |
| 291 | PhCH₂OC(O)− | H₂NCH₂CH₂CH₂CH₂− | CH₃CH₂CH₂CH₂− | 3 | 2,5-dihydrofuran |
| 292 | PhCH₂OC(O)− | CH₃C(O)N(H)(CH₂)₄− | CH₃CH₂CH₂CH₂− | 3 | 2,5-dihydrofuran |
| 293 | PhCH₂OC(O)− | PhCH₂− | CH₃CH₂CH₂CH₂− | 3 | 2,5-dihydrofuran |
| 294 | PhCH₂OC(O)− | 4-CH₃O-C₆H₄-CH₂− | CH₃CH₂CH₂CH₂− | 3 | 2,5-dihydrofuran |
| 295 | PhCH₂OC(O)− | 4-HO-C₆H₄-CH₂− | CH₃CH₂CH₂CH₂− | 3 | 2,5-dihydrofuran |
| 296 | PhCH₂OC(O)− | PhCH₂CH₂− | CH₃CH₂CH₂CH₂− | 3 | 2,5-dihydrofuran |
| 297 | PhCH₂OC(O)− | (CH₃)₂CHCH₂− | CH₃CH₂CH₂CH₂− | 3 | 2,3-dihydrofuran |

TABLE 2-continued (n = 1)

| Comp. No. | R¹ | R² | R³ | m | —C⟨⟩X |
|---|---|---|---|---|---|
| 298 | 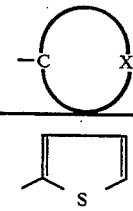 PhCH₂OC(=O)— | (CH₃)₂CHCH₂— | CH₃CH₂CH₂CH₂— | 3 | 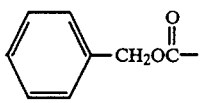 (S) |
| 299 | (CH₃)₃COC(=O)— | (CH₃)₂CHCH₂— | CH₃CH₂CH₂CH₂— | 3 | 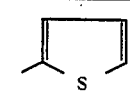 (S) |
| 300 | 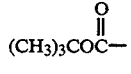 PhCH₂OC(=O)— | (CH₃)₂CHCH₂— | CH₃CH₂CH₂CH₂— | 3 | 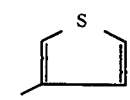 (S) |
| 301 | H | (CH₃)₂CHCH₂— | CH₃CH₂CH₂CH₂— | 3 | 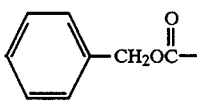 (S) |
| 302 | 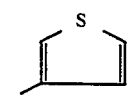 PhOCH₂C(=O)— | (CH₃)₂CHCH₂— | CH₃CH₂CH₂CH₂— | 3 | 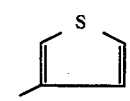 (S) |
| 303 | 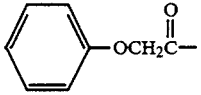 4-CH₃O-C₆H₄-OCH₂C(=O)— | (CH₃)₂CHCH₂— | CH₃CH₂CH₂CH₂— | 3 | 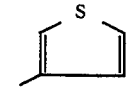 (S) |
| 304 | 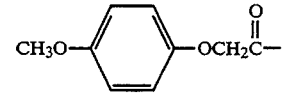 4-CF₃-C₆H₄-OCH₂C(=O)— | (CH₃)₂CHCH₂— | CH₃CH₂CH₂CH₂— | 3 | 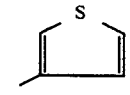 (S) |
| 305 | 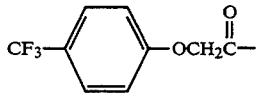 PhCH₂OC(=O)— | (CH₃)₂CHCH₂— | CH₃CH₂CH₂CH₂— | 4 | 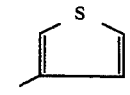 (O) |
| 306 | 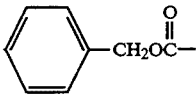 PhCH₂OC(=O)— | (CH₃)₂CHCH₂— | CH₃CH₂CH₂CH₂— | 4 | 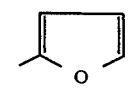 (O) |
| 307 | 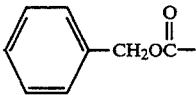 PhCH₂OC(=O)— | (CH₃)₂CHCH₂— | CH₃CH₂CH₂CH₂— | 4 | 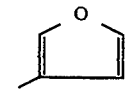 (S) |
| 308 | 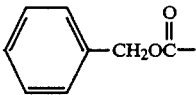 PhCH₂OC(=O)— | (CH₃)₂CHCH₂— | CH₃CH₂CH₂CH₂— | 4 | 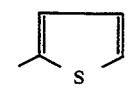 (S) |
| 309 | 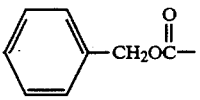 PhCH₂OC(=O)— | (CH₃)₂CHCH₂— | CH₃CH₂CH₂CH₂— | 5 | 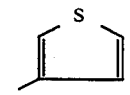 (O) |
| 310 | 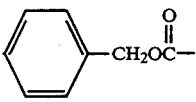 PhCH₂OC(=O)— | (CH₃)₂CHCH₂— | CH₃CH₂CH₂CH₂— | 5 | 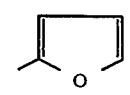 (O) |

TABLE 2-continued (n = 1)

| Comp. No. | R¹ | R² | R³ | m | —C⟨X⟩ |
|---|---|---|---|---|---|
| 311 | PhCH₂OC(O)— | (CH₃)₂CHCH₂— | CH₃CH₂CH₂CH₂— | 5 | 2-thienyl |
| 312 | PhCH₂OC(O)— | (CH₃)₂CHCH₂— | CH₃CH₂CH₂CH₂— | 5 | 3-thienyl |
| 313 | PhCH₂OC(O)— | (CH₃)₂CHCH₂— | cyclohexyl-CH₂— | 3 | 2-furyl |
| 314 | PhCH₂OC(O)— | (CH₃)₂CHCH₂— | cyclohexyl-CH₂— | 3 | 3-furyl |
| 315 | PhCH₂OC(O)— | (CH₃)₂CHCH₂— | cyclohexyl-CH₂— | 3 | 2-thienyl |
| 316 | PhCH₂OC(O)— | (CH₃)₂CHCH₂— | cyclohexyl-CH₂— | 3 | 3-thienyl |
| 317 | PhCH₂OC(O)— | CH₃— | PhCH₂— | 3 | 2-furyl |
| 318 | PhCH₂OC(O)— | (CH₃)₂CH— | PhCH₂— | 3 | 2-furyl |
| 319 | (CH₃)₃COC(O)— | (CH₃)₂CHCH₂— | PhCH₂— | 3 | 2-furyl |
| 320 | cyclohexyl-CH₂OC(O)— | (CH₃)₂CHCH₂— | PhCH₂— | 3 | 2-furyl |
| 321 | PhCH₂OC(O)— | (CH₃)₂CHCH₂— | PhCH₂— | 3 | 2-furyl |
| 322 | (2-pyridyl)CH₂OC(O)— | (CH₃)₂CHCH₂— | PhCH₂— | 3 | 2-furyl |

TABLE 2-continued (n = 1)

| Comp. No. | R¹ | R² | R³ | m | —C⌒X |
|---|---|---|---|---|---|
| 323 | 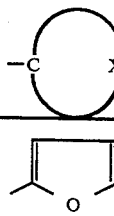 (3-pyridyl-CH₂OC(O)—) | (CH₃)₂CHCH₂— | 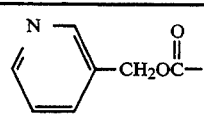 Ph-CH₂— | 3 | 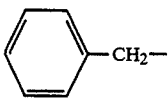 (2-furyl) |
| 324 | 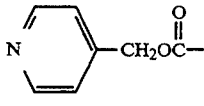 (4-pyridyl-CH₂OC(O)—) | (CH₃)₂CHCH₂— | 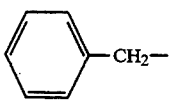 Ph-CH₂— | 3 | 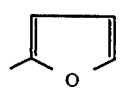 (2-furyl) |
| 325 | H | (CH₃)₂CHCH₂— | 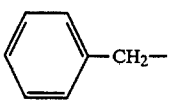 Ph-CH₂— | 3 | 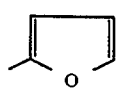 (2-furyl) |
| 326 | 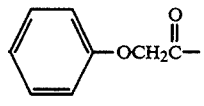 (PhOCH₂C(O)—) | (CH₃)₂CHCH₂— | 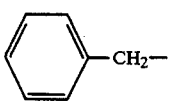 Ph-CH₂— | 3 | 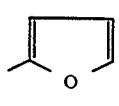 (2-furyl) |
| 327 | 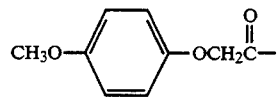 (4-CH₃O-PhOCH₂C(O)—) | (CH₃)₂CHCH₂— | 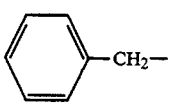 Ph-CH₂— | 3 | 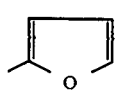 (2-furyl) |
| 328 | 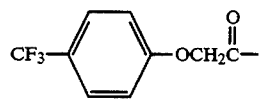 (4-CF₃-PhOCH₂C(O)—) | (CH₃)₂CHCH₂— | 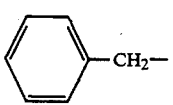 Ph-CH₂— | 3 | 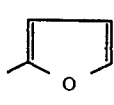 (2-furyl) |
| 329 | 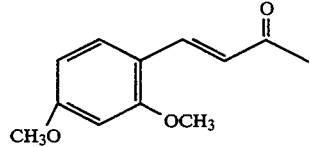 (2,4-diOMe-cinnamoyl-methyl) | (CH₃)₂CHCH₂— | 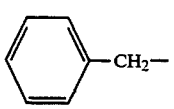 Ph-CH₂— | 3 | 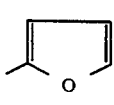 (2-furyl) |
| 330 | 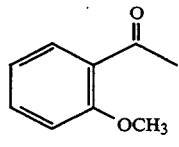 (2-OMe-acetyl-Ph) | (CH₃)₂CHCH₂— | 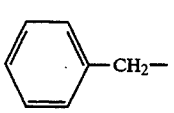 Ph-CH₂— | 3 | 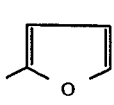 (2-furyl) |
| 331 | 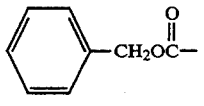 (PhCH₂OC(O)—) | 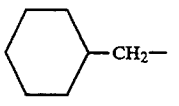 cyclohexyl-CH₂— | 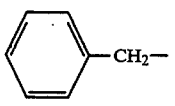 Ph-CH₂— | 3 | 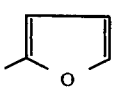 (2-furyl) |
| 332 | 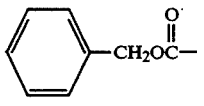 (PhCH₂OC(O)—) | (CH₃)₂CHCH₂— | 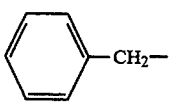 Ph-CH₂— | 3 | 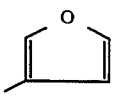 (3-furyl) |
| 333 | 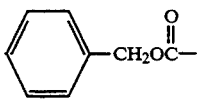 (PhCH₂OC(O)—) | (CH₃)₂CHCH₂— | 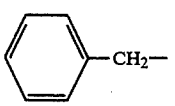 Ph-CH₂— | 3 | 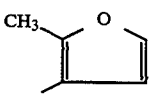 (2,3-dimethylfuryl variant) |
| 334 | 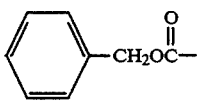 (PhCH₂OC(O)—) | (CH₃)₂CHCH₂— | 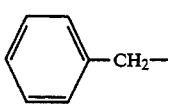 Ph-CH₂— | 3 | 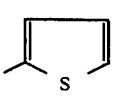 (2-thienyl) |

TABLE 2-continued
(n = 1)
| Comp. No. | R¹ | R² | R³ | m | —C⟨⟩X |
|---|---|---|---|---|---|
| 335 | 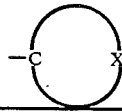 | (CH₃)₂CHCH₂— | 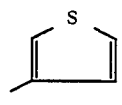 | 3 | 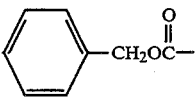 |
| 336 | (CH₃)₃COC(=O)— | (CH₃)₂CHCH₂— | 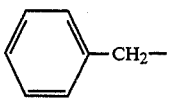 | 3 | 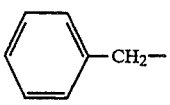 |
| 337 | 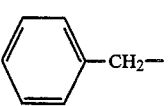 | (CH₃)₂CHCH₂— | 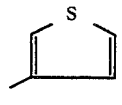 | 3 | 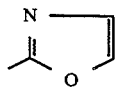 |
| 338 | 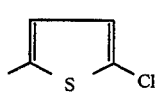 | (CH₃)₂CHCH₂— | 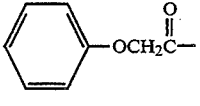 | 3 | 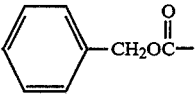 |
| 339 | H | (CH₃)₂CHCH₂— | 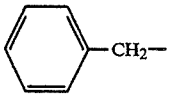 | 3 | 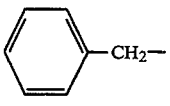 |
| 340 | 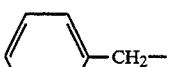 | (CH₃)₂CHCH₂— | 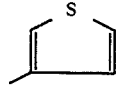 | 3 | 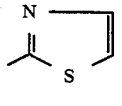 |
| 341 | 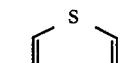 | (CH₃)₂CHCH₂— | 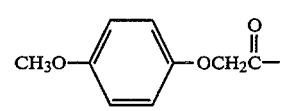 | 3 | 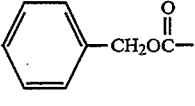 |
| 342 | 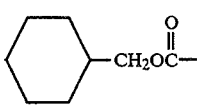 | (CH₃)₂CHCH₂— | 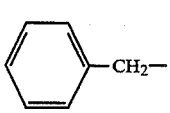 | 3 | 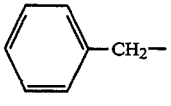 |
| 343 | 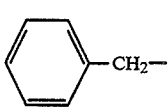 | (CH₃)₂CHCH₂— | 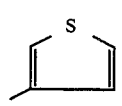 | 3 | 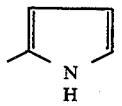 |
| 344 | 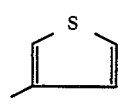 | (CH₃)₂CHCH₂— | 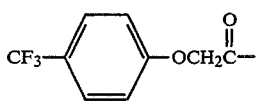 | 3 | 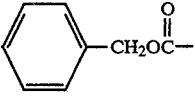 |
| 345 | 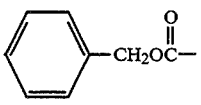 | (CH₃)₂CHCH₂— | 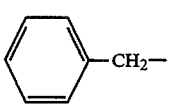 | 3 | 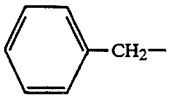 |
| 346 | 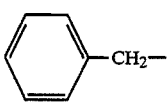 | (CH₃)₂CHCH₂— | 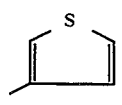 | 3 | 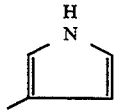 |

TABLE 2-continued
(n = 1)
| Comp. No. | R¹ | R² | R³ | m | —C‹X |
|---|---|---|---|---|---|
| 347 | 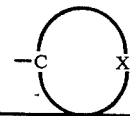 | (CH₃)₂CHCH₂— | 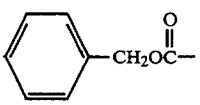 F—⟨⟩—CH₂— | 3 | 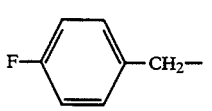 |
| 348 | 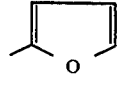 | (CH₃)₂CHCH₂— | F—⟨⟩—CH₂— | 3 | 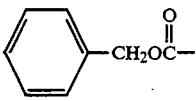 |
| 349 | 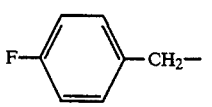 | (CH₃)₂CHCH₂— | F—⟨⟩—CH₂— | 3 | 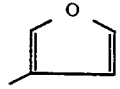 |
| 350 | 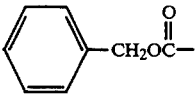 | (CH₃)₂CHCH₂— | F—⟨⟩—CH₂— | 3 | 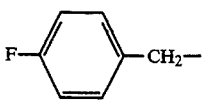 |
| 351 | 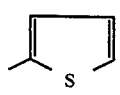 | (CH₃)₂CHCH₂— | Cl—⟨⟩—CH₂— | 3 | 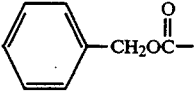 |
| 352 | 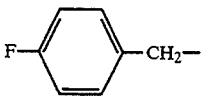 | (CH₃)₂CHCH₂— | Cl—⟨⟩—CH₂— | 3 | 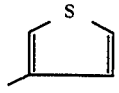 |
| 353 | 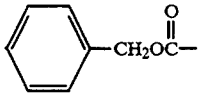 | (CH₃)₂CHCH₂— | Cl—⟨⟩—CH₂— | 3 | 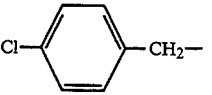 |
| 354 | 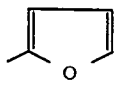 | (CH₃)₂CHCH₂— | Cl—⟨⟩—CH₂— | 3 | 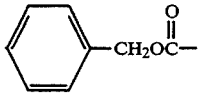 |
| 355 | 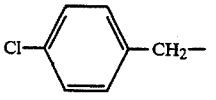 | (CH₃)₂CHCH₂— | CH₃O—⟨⟩—CH₂— | 3 | 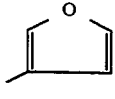 |
| 356 | 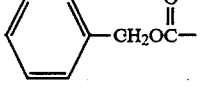 | (CH₃)₂CHCH₂— | CH₃O—⟨⟩—CH₂— | 3 | 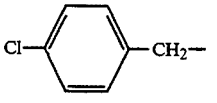 |
| 357 | 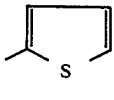 | (CH₃)₂CHCH₂— | CH₃O—⟨⟩—CH₂— | 3 | 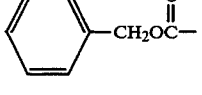 |
| 358 | 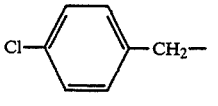 | (CH₃)₂CHCH₂— | CH₃O—⟨⟩—CH₂— | 3 | 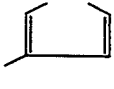 |

TABLE 2-continued (n = 1)

| Comp. No. | R¹ | R² | R³ | m | -C-X ring |
|---|---|---|---|---|---|
| 359 | PhCH$_2$OC(=O)- | (CH$_3$)$_2$CHCH$_2$- | 4-HO-C$_6$H$_4$-CH$_2$- | 3 | 2-furyl |
| 360 | PhCH$_2$OC(=O)- | (CH$_3$)$_2$CHCH$_2$- | 4-HO-C$_6$H$_4$-CH$_2$- | 3 | 3-furyl |
| 361 | PhCH$_2$OC(=O)- | (CH$_3$)$_2$CHCH$_2$- | 4-HO-C$_6$H$_4$-CH$_2$- | 3 | 2-thienyl |
| 362 | PhCH$_2$OC(=O)- | (CH$_3$)$_2$CHCH$_2$- | 4-HO-C$_6$H$_4$-CH$_2$- | 3 | 3-thienyl |
| 363 | (CH$_3$)$_3$COC(=O)- | (CH$_3$)$_2$CHCH$_2$- | PhCH$_2$CH$_2$- | 3 | 2-furyl |
| 364 | C$_6$H$_{11}$-CH$_2$OC(=O)- | (CH$_3$)$_2$CHCH$_2$- | PhCH$_2$CH$_2$- | 3 | 2-furyl |
| 365 | PhCH$_2$OC(=O)- | (CH$_3$)$_2$CHCH$_2$- | PhCH$_2$CH$_2$- | 3 | 2-furyl |
| 366 | 4-F-C$_6$H$_4$-CH$_2$OC(=O)- | (CH$_3$)$_2$CHCH$_2$- | PhCH$_2$CH$_2$- | 3 | 2-furyl |
| 367 | H | (CH$_3$)$_2$CHCH$_2$- | PhCH$_2$CH$_2$- | 3 | 2-furyl |
| 368 | PhOCH$_2$C(=O)- | CH$_3$)$_2$CHCH$_2$- | PhCH$_2$CH$_2$- | 3 | 2-furyl |
| 369 | 2-OCH$_3$-C$_6$H$_4$-OCH$_2$C(=O)- | CH$_3$)$_2$CHCH$_2$- | PhCH$_2$CH$_2$- | 3 | 2-furyl |
| 370 | 4-CH$_3$O-C$_6$H$_4$-OCH$_2$C(=O)- | (CH$_3$)$_2$CHCH$_2$- | PhCH$_2$CH$_2$- | 3 | 2-furyl |

TABLE 2-continued (n = 1)

| Comp. No. | R¹ | R² | R³ | m | −C⟨X |
|---|---|---|---|---|---|
| 371 | 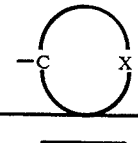 (4-CF₃-phenyl-OCH₂C(O)−) | (CH₃)₂CHCH₂− | 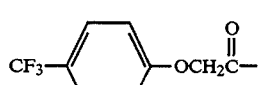 (phenyl-CH₂CH₂−) | 3 | 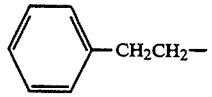 (furan) |
| 372 | 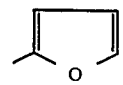 (phenyl-C(O)CH₃, acetophenone) | (CH₃)₂CHCH₂− | 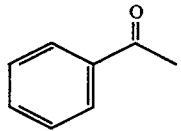 | 3 | 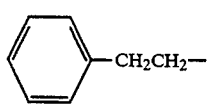 (furan) |
| 373 | 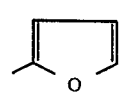 (2-OCH₃-phenyl-C(O)−) | (CH₃)₂CHCH₂− | 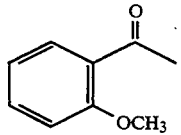 | 3 | 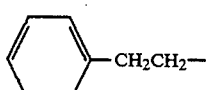 (furan) |
| 374 | 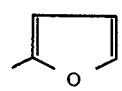 (4-CH₃O-phenyl-C(O)−) | (CH₃)₂CHCH₂− | 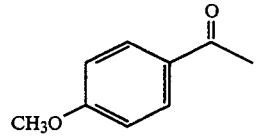 | 3 | 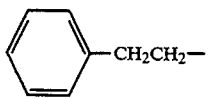 (furan) |
| 375 | 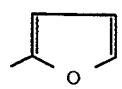 (phenyl-CH₂OC(O)−) | (CH₃)₂CHCH₂− | 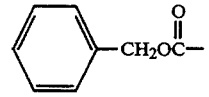 | 3 | 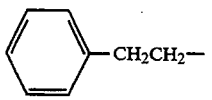 (furan) |
| 376 | 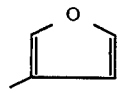 (phenyl-CH₂OC(O)−) | (CH₃)₂CHCH₂− | 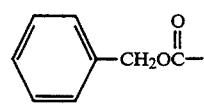 | 3 | 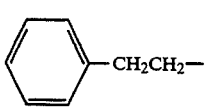 (thiophene) |
| 377 | 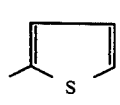 (phenyl-CH₂OC(O)−) | (CH₃)₂CHCH₂− | 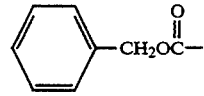 | 3 | 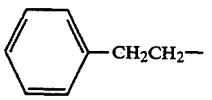 (thiophene) |
| 378 | (CH₃)₃COC(O)− | (CH₃)₂CHCH₂− | 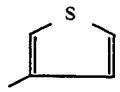 | 3 | 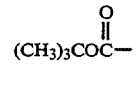 (thiophene) |
| 379 | H | (CH₃)₂CHCH₂− | 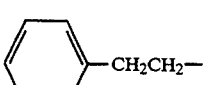 | 3 | 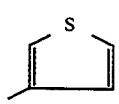 (thiophene) |
| 380 | 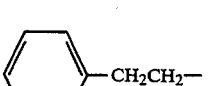 (phenyl-OCH₂C(O)−) | (CH₃)₂CHCH₂− | 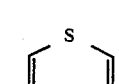 | 3 | 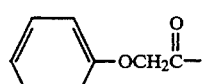 (thiophene) |
| 381 | 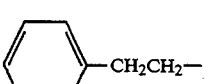 (4-CH₃O-phenyl-OCH₂C(O)−) | (CH₃)₂CHCH₂− | 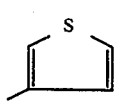 | 3 | 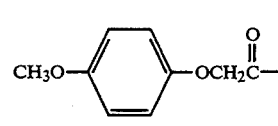 (thiophene) |

TABLE 2-continued (n = 1)

| Comp. No. | R¹ | R² | R³ | m | -C◯X |
|---|---|---|---|---|---|
| 382 | CH₃O-C₆H₃(OCH₃)-CH=CH-CO-CH₃ (2-OCH₃, 4-CH₃O) | $(CH_3)_2CHCH_2-$ | C₆H₅-CH₂CH₂- | 3 | thiophene |
| 383 | $(CH_3)_3COC(O)-$ | $(CH_3)_2CHCH_2-$ | $CH_3CH_2CH_2CH_2-$ | 3 | thiophene |
| 384 | H | $(CH_3)_2CHCH_2-$ | $CH_3CH_2CH_2CH_2-$ | 3 | thiophene |
| 385 | C₆H₅-O-CH₂-C(O)- | $(CH_3)_2CHCH_2-$ | $CH_3CH_2CH_2CH_2-$ | 3 | thiophene |
| 386 | $CH_3O$-C₆H₄-O-CH₂-C(O)- | $(CH_3)_2CHCH_2-$ | $CH_3CH_2CH_2CH_2-$ | 3 | thiophene |
| 387 | $CF_3$-C₆H₄-O-CH₂-C(O)- | $(CH_3)_2CHCH_2-$ | $CH_3CH_2CH_2CH_2-$ | 3 | thiophene |
| 388 | F-C₆H₄-C(O)- | $(CH_3)_2CHCH_2-$ | $CH_3CH_2CH_2CH_2-$ | 3 | thiophene |

A method of preparing the compound according to the present invention is now described. Alpha-aminoketone derivatives having the aforementioned general formula (I) my be prepared through, but not limited to, the following method.

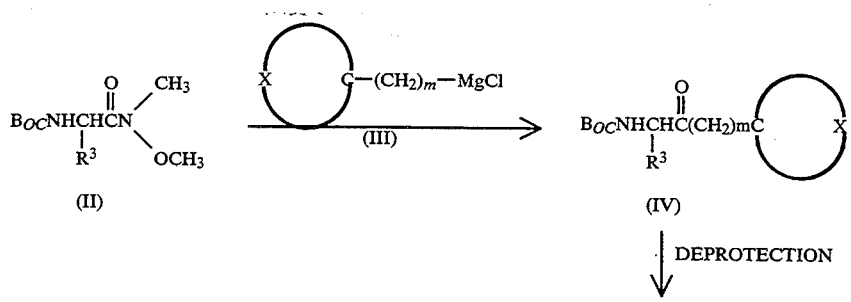

$$BocNHCHCHC(O)N(CH_3)(OCH_3) \quad + \quad X{-}C{-}(CH_2)_m{-}MgCl \longrightarrow BocNHCHC(O)(CH_2)_m C{-}X$$
$$(II) \qquad\qquad (III) \qquad\qquad (IV)$$

↓ DEPROTECTION

-continued

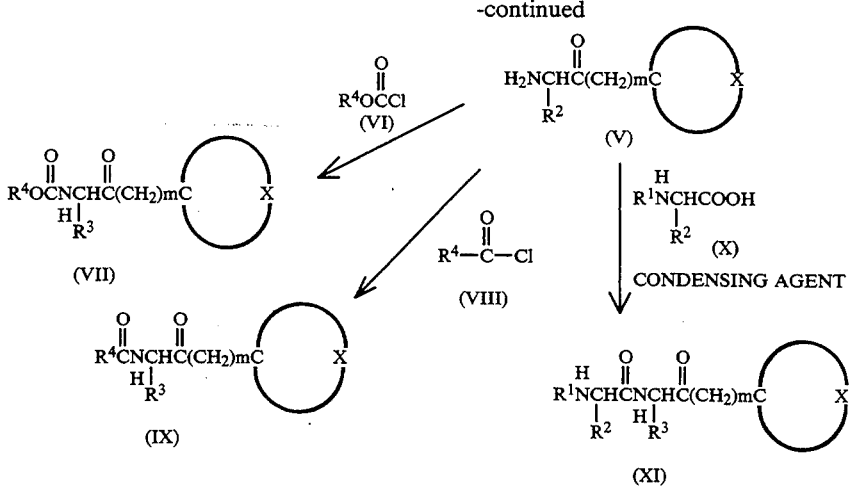

In the above mentioned general formula (I), R¹, R², R³, R⁴,

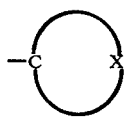

and m are as hereinabove defined while Boc is a tert-butoxycarbonyl group.

A hydroxamic acid derivative having the formula (II), prepared through a known method as disclosed in Synthesis, p.676, (1983), is dissolved in a solvent such as diethylether, tetrahydrofuran or dimethoxyethane, which is subjected to the Grignard reaction at −78° to 0° C. with a Grignard reagent having the formula (III). The reactant is then post-treated with an acid such as a dilute hydrochloric acid, which produces a compound having the formula (IV). Subsequently, the Boc group of the compound (IV) is treated in any one of common methods to provide the aminoketone derivative having the formula (V) or their salts. Such methods include treatment of the Boc group using, for example, hydrochloric acid-ethanol, hydrogen chloride containing ethyl acetate, hydrogen chloride containing dioxane, hydrogen chloride containing ethanol or hydrogen bromide containing acetic acid. The compound (V) is dissolved in a solvent such as diethylether, tetrahydrofuran, dioxane, ethyl acetate, dichloromethane, chloroform, 1,2-dichloroethane, dimethylformamide or N-methylpyrrolidone, which is then reacted with the chloroformate derivative having the formula (VI) in the presence of a base such as triethylamine or pyridine. This results in production of the compound having the formula (VII). Reaction of the compound (V) with acid chloride having the formula (VIII) provides the compound having the formula (IX). On the other hand, the compound having the formula (XI) is produced when the compound (V) and the carboxyl group of the amino acid derivative having the formula (X) are activated with a condensing agent such as isobutyl chloroformate, diphenylphosphoryl azide, carbonyldiimidazole or dicyclohexylcarbodiimide in the presence of a base such as triethylamine or pyridine, if necessary, and reacted with each other in the presence of a base such as triethylamine or pyridine.

For applying the compound according to the present invention to the clinical fields, the ratio of the therapeutically active component relative to the carrier can be altered within the range between 1% to 99% by weight. For example, the compound according to the present invention may be formed into various dosage forms for oral administration. Such dosage forms include granules, fine granules, powders, tablets, hard gelatin capsules, soft elastic capsules, syrup, emulsion, suspension and liquid preparation. Alternatively, the compound may be used as parenteral injections for intravenous, intramuscular or subcutaneous injections. It may also be used as a suppository. In addition, the compound may be formed into powders for injection and prepared whenever it becomes necessary. The drug according to the present invention can be prepared with adequate organic or inorganic medical diluent and/or solid or liquid carrier suitable for oral, rectal or parenteral administration. The vehicles, fillers, diluents and excipient preferably used for solid preparation are: lactose, sucrose, starch, talc, cellulose, dextrin, kaolin and calcium carbonate. The liquid preparation for oral administration, i.e., emulsion, syrup and suspension include commonly used inactive diluent such as water and vegetable oil. The preparation may contain, other than the inactive diluent, auxiliaries such as moistening agents, suspending agents, sweetening agents, aromatic agents, coloring agents and preservatives. Alternatively, the preparation may be contained in, as the liquid preparation, a capsule made of an absorbed material such as gelatin. Examples of the solvents and suspending agents preferably used for preparing the preparation for the parenteral administration, i.e., injection and suppository are: water, propylene glycol, polyethylene glycol, benzyl alcohol, ethyl oleate and lecithin. Exemplified bases for the suppository include cacao butter, emulsificated cacao butter, laurin tallow and witepsol. The preparation can be made according to any one of ordinary methods.

The dosage relating to the present compound for oral administration to adults is generally in the range of between 0.01 to 1,000 mg as the daily dose. It is, however, preferable to control the dosage depending on the age, the degree of diseases and the symptom. The daily dose of the drug according to the present invention may be administered once a day. The same dose may also be administered two or three times a day at suitable intervals or on alternate days or so.

The daily dose of 0.001 to 100 mg relating to the present compound for injection to adults is preferably administered continuously or intermittently.

The foregoing features of the present invention will be more readily apparent in the context of a specifically delineated set of examples and a reference. However, it should be understood that the present invention is not limited to those particular examples and the reference as long as not being depart from the spirit and scope of the appended claims.

REFERENCE 1

Preparation of 1-chloro-4-(2-furyl)butane

Furan (1.36 g) was dissolved in tetrahydrofuran (50 ml) and cooled to −25° C. Hexane solution (12.5 ml) of n-butyllithium of 1.68 mol/l was added to the reaction solution, which was stirred at −15° C. for 4 hours. Subsequently, 1-bromo-4-chlorobutane (3.43 g) was dissolved in tetrahydrofuran (2.5 ml) and added to the reaction solution. This solution was further stirred at −15° C. for 1 hour and stood overnight at room temperature. The reaction solution was poured into icy water and extracted with ether. The extracted solution was successively washed with water, a saturated ammonium chloride solution and a saturated sodium chloride solution. It was then dried over magnesium sulfate and filtered. The filtrate was concentrated and the resultant oil-like product was purified by distillation under reduced pressure (130° C./12 mmHg). The object compound (2.87 g) was obtained in the form of oil.

Yield: 91% NMR (CDCl$_3$, δ): 1.80(m, 4H), 2.66(t, J=6.5 Hz, 2H), 3.55(t, J=6.3 Hz, 2H), 6.00(dd, J=2.4 Hz, 0.8 Hz, 1H), 6.28(m, 1H), 7.30(dd, J=1.8 Hz, 0.6 Hz, 1H).

EXAMPLE 1

Preparation of (S)-6-tert-butoxycarbonylamino-1-(2-furyl)-5-decanone (Compound No. 73 in Table 1)

Metal magnesium turnings (869 mg) were added to ether (5 ml), to which 1-chloro-4-(2-furyl)butane (2.87 g) obtained in the Reference 1 in ether (3 ml) was added dropwise. A drop of 1,2-dibromoethane was added to the reaction solution, which was refluxed gently for 2 hours. The reaction solution was then cooled to −20° C., to which N-tert-butoxycarbonyl-N′-methoxy-N′-methyl L-norleucineamido (1.24g) dissolved in ether (3 ml) was added dropwise. The reaction solution was stirred at −15° C. for 1 hour and further stirred at 0° C. for 1.5 hours. This solution was poured into a cooled solution of 1N hydrochloric acid and extracted with ether. The extracted solution was successively washed with water, a saturated sodium hydrogencarbonate solution and a saturated sodium chloride solution. It was dried over magnesium sulfate and filtered. The filtrate was concentrated and purified by the silica gel column chromatography (eluent hexane:ethyl acetate 6:1). The object compound (1.33 g) was obtained in the form of oil.

Yield: 87% IR: (KBr, cm$^{-1}$): 3356, 1707, 1508 NMR (CDCl$_3$, δ): 0.89(m, 3H), 1.13–1.40(m, 1H), 1.44(s, 9H), 1.52(m, 1H), 1.57–1.68(m, 4H), 1.80(m, 1H), 2.50(m, 2H), 2.63(m, 2H), 4.29(m, 1H), 5.16(d, J=7.1 Hz, 1H), 5.98(dd, J=3.2 Hz, 0.8 Hz, 1H), 6.27(dd, J=3.1 Hz, 1.9 Hz, 1H), 7.29(dd, J=1.8 Hz, 0.8 Hz, 1H)

EXAMPLE 2

Preparation of (S)-6-amino-1-(2-furyl)-5-decanone hydrochloride (Compound No. 75 in Table 1)

(S)-6-tert-Butoxycarbonylamino-1-(2-furyl)-5-decanone (214 mg) obtained in Example 1 was dissolved in 2 ml solution of ethyl acetate containing 4N hydrogen chloride and stirred for 20 minutes. Then, n-hexane (10 ml) was added to the reaction solution, which was concentrated to dryness to obtain the object compound.

NMR (CDCl$_3$, δ): 0.96(t, J=6.8 Hz, 3H), 1.10–1.30(m, 4H), 1.30–1.75(m, 4H), 1.80(m, 1H), 1.99(m, 1H), 2.50–2.75(m, 4H), 4.12(dd, J=7.4 Hz, 4.2 Hz, 1H), 6.02(dd, J=3.2 Hz, 0.7 Hz, 1H), 6.27(dd, J=3.0 Hz, 2.0 Hz, 1H), 7.32(t, J=1.1Hz,

EXAMPLE 3

Preparation of (S)-6-((S)-2-benzyloxycarbonylamino-4-methyl-valerylamino)-1-(2-furyl)-5-decanone (Compound No. 305 in Table 2)

N-Benzyloxycarbonyl-L-leucine (185 mg) was dissolved in methylene chloride (5 ml) and cooled to −5° C., to which triethylamine (70 mg) and isobutyl chloroformate (87 mg) were added. The resultant solution was stirred for 15 minutes. Added thereto were triethylamine (64 mg) and a solution of (S)-6-amino1-(2-furyl)-5-decanone hydrochloride obtained in Example 2 dissolved in methylene chloride (3 ml). One hour later, 0.5N hydrochloric acid solution (10 ml) was added thereto, which was then extracted with methylene chloride. The extracted solution was successively washed with water, a saturated sodium hydrogencarbonate solution and a saturated sodium chloride solution. It was dried over magnesium sulfate and filtered. The filtrate was concentrated and purified by the silica gel column chromatography (eluent hexane:ethyl acetate 4:1). The resultant product was re-crystallized from a mixed solution of hexane and ethyl acetate to obtain the object compound (199 mg).

Yield: 65% Melting Point: 92°–93° C. IR: (KBr, cm$^{-1}$): 3306, 1690, 1625, 1535 NMR (CDCl$_3$, δ): 0.87(t, J=6.6 Hz, 3H), 0.94(d, J=5.8 Hz, 6H), 1.06–1.20(m, 4H), 1.20–1.73(m, 8H), 1.85(m, 1H), 2.50(m, 2H), 2.63(m, 2H), 4.19(m, 1H), 4.56(ddd, J=7.2 Hz, 7.2 Hz, 4.6 Hz, 1H), 5.11 (s, 2H), 5.14(s, 1H), 5.98(d, J=3.1 Hz, 1H), 6.27(s, 1H), 6.57(d, J=6.4 Hz, 1H), 7.29 (d, J=0.9 Hz, 1H), 7.35(s, 5H)

Similar operations were repeated to those made in Reference 1 and Examples 1 through 3 to prepare the following compounds. Values of physical properties thereof are shown below.

EXAMPLE 4

Preparation of (S)-5-tert-butoxycarbonylamino-1-(2-furyl)-4-nonanone (Compound No. 53 in Table 1)

NMR (CDCl$_3$, δ): 0.89(t, J=7.1 Hz, 3H), 1.12–1.58(m, 5H), 1.44(s, 9H), 1.81(m, 1H), 1.95(m, 2H), 2.53(m, 2H), 2.65(t, J=7.3 Hz, 2H), 4.26(m, 1H), 5.17(d, J=7.3 Hz, 1H), 5.99(d, J=3.1 Hz, 1H), 6.27(m, 1H), 7.29(m, 1H)

EXAMPLE 5

Preparation of (S)-5-((S)-2-benzyloxycarbonylamino-4-methyl-valerylamino)-1-(2-furyl)-4-nonanone (Compound No. 257 in Table 2)

Melting Point: 62°-64° C. IR: (KBr, cm$^{-1}$): 3283, 1721, 1686, 1655, 1535 NMR (CDCl$_3$, δ): 0.86(t, J=6.8 Hz, 3H), 0.94(d, J=6.1 Hz, 6H), 1.07-1.40(m, 4H), 1.40-1.72(m, 1H), 1.85(m, 1H), 1.94(t, J=7.1 Hz, 2H), 2.44-2.58(m, 2H), 2.65(t, J=7.1 Hz, 2H), 5.99(dd, J=3.1 Hz, 0.6 Hz, 1H), 6.27(dd, J=3.2 Hz, 2.0 Hz, 1H), 6.58(d, J=7.2 Hz, 1H), 7.30(dd, J=1.8 Hz, 0.7 Hz, 1H), 7.35(s, 5H)

EXAMPLE 6

Preparation of (S)-5-benzyloxycarbonylamino-1-(2-furyl)-4-nonanone (Compound No. 55 in Table 1)

NMR (CDCl$_3$, δ): 0.87(t, J=6.7 Hz, 3H), 1.07-1.40(m, 4H), 1.43-1.61(m, 1H), 1.66-2.01(m, 3H), 2.38-2.58(m, 2H), 2.64(t, J=7.2 Hz, 2H), 4.36(m, 1H), 5.09(s, 2H), 5.46(d, J=7.5 Hz, 1H), 5.98(d, J=2.8 Hz, 1H), 6.26(m, 1H), 7.23-7.41(m, 6H)

EXAMPLE 7

Preparation of (S)-5-tert-butoxycarbonylamino-1-(2-thienyl)-4-nonanone (Compound No. 64 in Table 1)

Melting Point: 50.5°-52.5° C. IR: (KBr, cm$^{-1}$): 3380, 1721, 1688 NMR (CDCl$_3$, δ): 0.88(t, J=7.1 Hz, 3H), 1.18-1.37(m, 4H), 1.43(s, 9H), 1.49(m, 1H), 1.76(m, 1H), 1.78(tt, J=7.3 Hz, 7.3 Hz, 2H), 2.53(t, J=7.0 Hz, 1H), 2.54(t, J=7.4 Hz, 1H), 2.85(t, J=7.3 Hz, 2H), 4.27(m, 1H), 5.14(d, J=6.5 Hz, 1H), 6.78(d, J=2.5 Hz, 1H), 6.92(dd, J=5.0 Hz, 3.4 Hz, 1H), 7.12(dd, J=5.1 Hz, 1.0 Hz, 1H)

EXAMPLE 8

Preparation of (S)-5-amino-1-(2-thienyl)-4-nonanone hydrochloride (Compound No. 66 in Table 1)

Melting Point: 75°-78° C. IR: (KBr, cm$^{-1}$): 2932, 1723 NMR (CD3OD, δ): 0.94(t, J=6.8 Hz, 3H), 1.20-1.50(m, 4H), 1.79(m, 1H), 1.90(m, 1H), 1.98(tt, J=7.2 Hz, 7.2 Hz, 2H), 2.64(t, J=7.3 Hz, 1H), 2.67(t, J=7.4 Hz, 1H), 2.88(t, J=7.3 Hz, 2H), 4.12(dd, J=7.5 Hz, 4.3 Hz, 1H), 6.82(dd, J=3.4 Hz, 0.9 Hz, 1H), 6.91(dd, J=5.0 Hz, 3.4 Hz, 1H), 7.19(dd, J=5.0 Hz, 1.1 Hz, 1H)

EXAMPLE 9

Preparation of (S)-5-((S)-2-benzyloxycarbonylamino-4-methyl-valerylamino)-1-(2-thienyl)-4-nonanone (Compound No. 298 in Table 2)

Melting Point: 65°-67° C. IR: (KBr, cm$^{-1}$): 3281, 1723, 1688, 1655 NMR (CDCl$_3$, δ): 0.86(t, J=6.7 Hz, 3H), 0.94(d, J=6.1 Hz, 6H), 1.10-1.40(m, 4H), 1.40-1.75(m, 3H), 1.79(m, 1H), 1.84(m, 1H), 1.98(tt, J=7.2 Hz, 7.2 Hz, 2H), 2.54(m, 2H), 2.85(t, J=7.3 Hz, 2H), 4.20(m, 1H), 4.54(m, 1H), 5.11(s, 2H), 5.17(d, J=7.6 Hz, 1H), 6.57(d, J=6.9 Hz, 1H), 6.78(d, J=2.6 Hz, 1H), 6.92(dd, J=5.1Hz, 3.4 Hz, 1H), 7.12(dd, J=5.1 Hz, 1.1 Hz, 1H), 7.34(s, 5H)

EXAMPLE 10

Preparation of (S)-5-((S)-2-tert-butoxycarbonylamino-4-methyl-valerylamino)-1-(2-thienyl)4-nonanone (Compound No. 383 in Table 2)

Melting Point: 70°-72° C. IR: (KBr, cm$^{-1}$): 3335, 1721, 1682, 1657 NMR (CDCl$_3$, δ): 0.87(t, J=6.7 Hz, 3H), 0.93(d, J=6.0 Hz, 3H), 0.94(d, J=6.2 Hz, 3H), 1.15-1.40(m, 4H), 1.44(s, 9H), 1.49(m, 1H), 1.58-1.69(m, 3H), 1.84(m, 1H), 1.98(tt, J=7.3 Hz, 7.3 Hz, 2H), 2.53(t, J=6.9 Hz, 1H), 2.55(t, J=7.5 Hz, 1H), 2.85(t, J=7.2 Hz, 1H), 4.11(m, 1H), 4.55(m, 1H), 4.88(d, J=7.1 Hz, 1H), 6.69(d, J=7.8 Hz, 1H), 6.78(d, J=3.3 Hz, 1H), 6.91(dd, J=5.1 Hz, 3.4 Hz, 1H), 7.12(dd, J=5.2 Hz, 1.1 Hz, 1H)

TEST EXAMPLE

Measurement of Inhibitory Activity against Calpain

Through the known method disclosed in Journal of Biological Chemistry, vol. 259, p.3210, (1984), m-calpain was purified from a brain of rat. The inhibitory activity against it was measured and determined according to the method disclosed in Journal of Biological Chemistry, vol. 259, p.12489 (1982). As a result, the 50% inhibitory concentration (IC$_{50}$) of the compound in Example 5 (Compound No. 257 in Table 2) was 10.1 μM.

What we claim is:

1. An α-aminoketone derivative of the following formula or a pharmaceutically acceptable salt thereof:

$$R^1 \left[ \begin{array}{c} H \\ N-CH-C \\ | \\ R^2 \end{array} \right]_n \begin{array}{c} H \\ N-CH-C-(CH_2)_m-C \\ | \\ R^3 \end{array} \bigcirc X, \quad (I)$$

wherein, R$^1$ is hydrogen, $$R^4-O-\overset{O}{\underset{\|}{C}}- \quad \text{or} \quad R^4-\overset{O}{\underset{\|}{C}}-$$

wherein R$^4$ is a member selected from the group consisting of (a) C$_1$ to C$_{20}$ alkyl which is unsubstituted or is substituted by at least one substituent selected from the group consisting of (1) C$_3$ to C$_8$ cycloalkyl, (2) C$_6$ to C$_{14}$ aryl which may be substituted by C$_1$ to C$_3$ alkoxy or a halogen atom, (3) a 5 or 6 membered heterocyclic group containing at least one hetero atom selected from the group consisting of nitrogen, sulfur and oxygen, (4) C$_3$ to C$_{15}$ cycloalkyloxy, (5) C$_6$ to C$_{14}$ aryloxy which may be substituted by C$_1$ to C$_3$ alkoxy, halogen or trifluoromethyl, (6) C$_7$ to C$_{20}$ aralkyloxy and (7) C$_6$ to C$_{14}$ arylthio, (b) C$_2$ to C$_{10}$ alkenyl which is unsubstituted or is substituted by C$_6$ to C$_{14}$ aryl which may be substituted by C$_1$ to C$_3$ alkoxy or C$_6$ to C$_{14}$ aryl which may be substituted by C$_1$ to C$_3$ alkoxy, halogen, C$_1$ to C$_3$ alkyl or trifluoromethyl, (c) C$_6$ to C$_{14}$ aryl which is unsubstituted or is substituted by C$_1$ to C$_3$ alkoxy, halogen, C$_1$ to C$_3$ alkyl or trifluoromethyl, and (d) a 5 or 6 membered heterocyclic group containing at least one hetero atom selected from the group consisting of nitrogen, sulfur and oxygen, $R^2$ and $R^3$ are independently hydrogen or $C_1$ to $C_{20}$ alkyl which is unsubstituted or is substituted by at least one member selected from the group consisting of (a) $C_3$ to $C_8$ cycloalkyl,
(b) $C_6$ to $C_{14}$ aryl which may be substituted by hydroxyl, $C_1$ to $C_6$ alkoxy or halogen,
(c) $C_1$ to $C_3$ alkylthio,
(d) hydroxyl,
(e) $C_1$ to $C_6$ alkoxy,
(f) $C_7$ to $C_{15}$ aralkyloxy,
(g) $C_2$ to $C_{10}$ alkoxycarbonyl,
(h) carboxyl,
(i) amino, and
(j) $C_2$ to $C_8$ alkanoylamino,

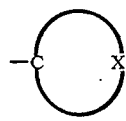

is a 5 to 6 membered heterocyclic group containing at least one hetero atom selected from the group consisting of nitrogen, sulfur and oxygen which heterocyclic group is unsubstituted or is substituted by halogen or $C_1$ to $C_3$ alkyl, n is 0 or 1, and m is an integer of 1 to 5.

2. A compound according to claim 1 wherein $R^1$ is hydrogen,

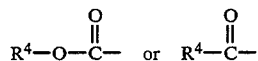

wherein $R^4$ is $C_1$ to $C_{10}$ alkyl which is unsubstituted or is substituted by at least one substituent selected from the group consisting of (1) $C_3$ to $C_8$ cycloalkyl, (2) $C_6$ to $C_{14}$ aryl which may be substituted by $C_1$ to $C_3$ alkoxy or halogen, (3) pyridyl, (4) $C_6$ to $C_{14}$ aryloxy which may be substituted by $C_1$ to $C_3$ alkoxy, halogen or trifluoromethyl, (5) $C_7$ to $C_{15}$ aralkyloxy and (6) $C_6$ to $C_{14}$ arylthio, $R^2$ and $R^3$ are independently $C_1$ to $C_{10}$ alkyl, and

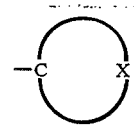

is furyl or thienyl.

3. A compound according to claim 1 wherein $R^1$ is hydrogen or

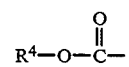

wherein $R^4$ is $C_1$ to $C_{10}$ alkyl which is unsubstituted or is substituted by $C_6$ to $C_{10}$ aryl, $R^2$ and $R^3$ are independently $C_1$ to $C_{10}$ alkyl, and

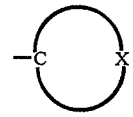

is furyl or thienyl.

4. A pharmaceutical composition for the treatment of diseases resulting from abnormal sthenia of thiol protease which comprises an effective amount of a compound or salt thereof as defined in claim 1 and a pharmaceutically acceptable carrier therefor.

5. A method for the treatment of a disease resulting from abnormal sthenia of thiol protease which comprises administering to a patient in need of such treatment an effective amount of a compound or salt thereof as defined in claim 1.

* * * * *